United States Patent [19]

Joshi et al.

[11] Patent Number: 6,051,123

[45] Date of Patent: Apr. 18, 2000

[54] MULTI-FUNCTIONAL AND $NO_X$ SENSOR FOR COMBUSTION SYSTEMS

[75] Inventors: Ashok Joshi, Sandy; Liang Jun Li; Anil Virkar, both of Salt Lake City, all of Utah; Meilin Liu, Norcross, Ga.

[73] Assignee: Gas Research Institute, Chicago, Ill.

[21] Appl. No.: 08/808,240

[22] Filed: Feb. 28, 1997

Related U.S. Application Data

[62] Continuation-in-part of application No. 08/482,958, Jun. 15, 1995, Pat. No. 5,667,652, which is a continuation of application No. 08/164,143, filed as application No. PCT/US93/11274, Nov. 19, 1993
[60] Provisional application No. 60/012,659, Mar. 1, 1996, and provisional application No. 60/014,627, Mar. 6, 1996.

[51] Int. Cl.⁷ .................................................. G01N 27/407
[52] U.S. Cl. .......................... 204/424; 204/412; 204/415; 204/426; 205/781
[58] Field of Search ................................... 204/412, 415, 204/421–429; 205/781

[56] References Cited

U.S. PATENT DOCUMENTS

| | | | |
|---|---|---|---|
| 3,514,377 | 5/1970 | Spacil et al. | 204/425 |
| 3,860,498 | 1/1975 | Jones | 204/425 |
| 3,989,614 | 11/1976 | Tien | 204/427 |
| 4,044,601 | 8/1977 | Sakurai et al. | 73/23 |
| 4,135,381 | 1/1979 | Sherwin | 73/23 |
| 4,151,503 | 4/1979 | Cermak et al. | 338/14 |
| 4,172,770 | 10/1979 | Semersky et al. | 204/415 |
| 4,190,499 | 2/1980 | Pebler | 205/784.5 |
| 4,272,331 | 6/1981 | Hetrick | 205/785 |
| 4,292,158 | 9/1981 | Muller et al. | 204/429 |
| 4,298,573 | 11/1981 | Fujishiro | 422/94 |
| 4,300,991 | 11/1981 | Chiba et al. | 204/412 |
| 4,305,724 | 12/1981 | Micko | 23/232 EC |
| 4,306,957 | 12/1981 | Ishitani et al. | 204/412 |
| 4,314,996 | 2/1982 | Sekido et al. | 422/98 |
| 4,345,985 | 8/1982 | Tohda et al. | 204/192 EC |
| 4,487,680 | 12/1984 | Logothetis et al. | 204/426 |
| 4,522,690 | 6/1985 | Venkatasetty | 205/783 |

(List continued on next page.)

FOREIGN PATENT DOCUMENTS

| | | |
|---|---|---|
| 25625 | 3/1981 | European Pat. Off. . |
| 3525774 | 1/1987 | Germany . |
| 55-99063 | 7/1980 | Japan . |
| 1076948 | 4/1986 | Japan . |
| 84552 | 4/1986 | Japan . |
| 225741 | 1/1990 | Japan . |
| 404348268 | 12/1992 | Japan . |
| 406160325 | 6/1994 | Japan . |

OTHER PUBLICATIONS

Liu et al., "Multifunctional Sensors Based on Ceramic Electrolytes," May 19, 1993.
Liu et al., "Characterization of Mixed Ionic–Electronic Conductors," published before Apr. 6, 1994.
Usui, T. et al., "Gas Polarographic Oxygen Sensor Using an Oxygen/Zirconia Electrolyte," J. Electrochem Soc., vol. 136, No. 2, pp. 534–542, Feb. 1989.
Heyne, L., "Some Properties and Applications of Zirconia–Based Solid–Electrolyte Cells," Eindhoven, pp. 65–88, Sep. 1974.
Logothetis, E.M., et al., "A High–Sensitivity Sensor for the Measurement of Combustible Gas Mixtures," Sensors and Conductors, 9, pp.363–372, 1986, month unavailable.
Liu, M., "Electrode Kinetics and Transport Properties of Mixed Ionic–Electronic Conductors," Ionic and Mixed Conducting Ceramics, PV–91–12, pp. 191–215, 1991, month available.

(List continued on next page.)

*Primary Examiner*—T. Tung
*Attorney, Agent, or Firm*—Factor and Shaftal

[57] ABSTRACT

A gas sensor is provided, having an electrolyte membrane, a sensing electrode, a counter electrode, a diffusion barrier for controlling access of gases to the sensing electrode, and in situ means for removing molecular oxygen from the gases to which the sensing electrode is being exposed.

2 Claims, 13 Drawing Sheets

U.S. PATENT DOCUMENTS

| | | | |
|---|---|---|---|
| 4,570,479 | 2/1986 | Sakurai et al. | 73/116 |
| 4,572,900 | 2/1986 | Wohltjen | 436/151 |
| 4,792,433 | 12/1988 | Katsura et al. | 422/98 |
| 4,832,818 | 5/1989 | Sekido et al. | 204/412 |
| 4,909,072 | 3/1990 | Logothetis et al. | 204/426 |
| 4,990,235 | 2/1991 | Chujo | 204/424 |
| 5,012,671 | 5/1991 | Yagawara et al. | 73/31.06 |
| 5,034,107 | 7/1991 | Wang et al. | 205/781 |
| 5,034,112 | 7/1991 | Murase et al. | 204/425 |
| 5,120,422 | 6/1992 | Liu et al. | 204/416 |
| 5,145,566 | 9/1992 | Logothetis et al. | 204/424 |
| 5,173,166 | 12/1992 | Tomantschger et al. | 204/412 |
| 5,217,588 | 6/1993 | Wang et al. | 205/781 |
| 5,226,309 | 7/1993 | Stetter et al. | 73/31.06 |
| 5,273,628 | 12/1993 | Liu et al. | 205/344 |
| 5,279,145 | 1/1994 | Suzuki | 73/23.32 |
| 5,397,442 | 3/1995 | Wachsman | 205/781 |
| 5,409,591 | 4/1995 | Baker et al. | 205/781 |

OTHER PUBLICATIONS

Liaw et al., "Low Temperature Limiting–Current Oxygen Sensors Based on Tetragonal Zirconia Polycrystals," J. Electrochem Soc., vol. 138, No. 8, Aug. 1991, pp. 2478–2483.

Liaw et al., "Novel Hydrogen Sensors for Use at Elevated Temperatures," Department of Material Science and Engineering, Stanford University, date unavailable.

Fukui et al., "CO Detection by BaO and $Y_2O_3$ Dispersed $SnO_2$ Ceramics," Symp Proc. on Chemical Sensors J. Electrochem. Soc., pp. 187–195, 1987, month unavailable.

Sandler, "The Response of the Stabilized Zirconia Galvanic Cell to Methane Oxygen Mixtures," Journal of the Electrochem. Society, Aug. 1971, vol. 118, No. 8, pp. 1378–1381.

Fujitsu et al., "$CO_2$ Gas Sensor Using (beta)–$Al_2O_3$ and Metal Carbonate," Journal of Materials Science Letters 5, 1986, month unavailable, pp. 285–286.

Heyne et al., "The Speed of Response of Solid Electrolyte Galvanic Cells for Gas Sensing," Journal of the Electrochem Society, vol. 124, No. 5, May 1977, pp. 727–735.

Uchida et al., "High Temperature Hydrogen Sensor and Steam Sensor Using $BaCeO_3$–Based Proton Conducting Ceramics," Tottori University, pp. 172–179, date unavailable.

Usui et al., "Solid State Humidity Sensor Usable at High Temperatures," Symp. Proc. on Chemical Sensors, J. Electrochem. Soc., pp. 202–211, 1987, month unavailable.

Logothetis, "$ZrO_2$ Oxygen Sensors in Automotive Applications," Advances in Ceramics, vol. 3, Science and Technology of Zirconia (The American Ceramic Society 1981), month unavailable.

EXPERIMENTALLY MEASURED CURRENT VS. VOLTAGE TRACE FOR A GAS MIXTURE CONTAINING 500 PPM OF $NO_x$, 2% OXYGEN, AND BALANCE NITROGEN. THE RAMP RATE WAS 0.1 VOLT/SEC.

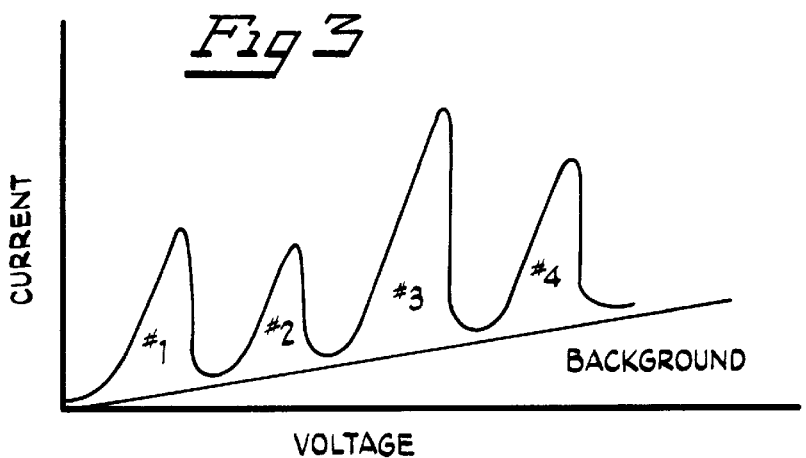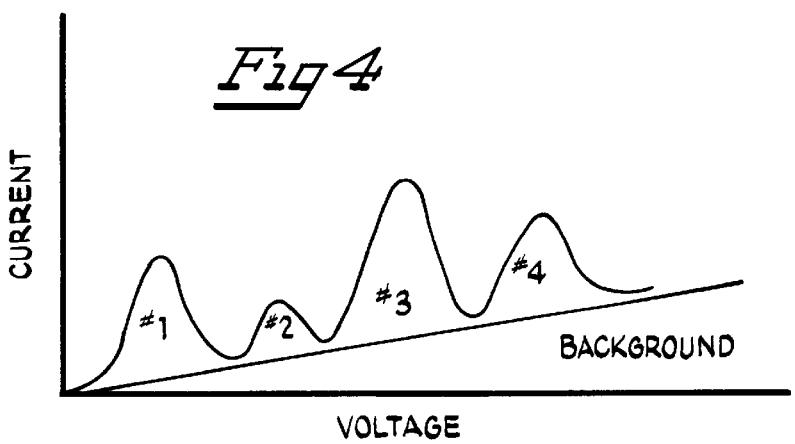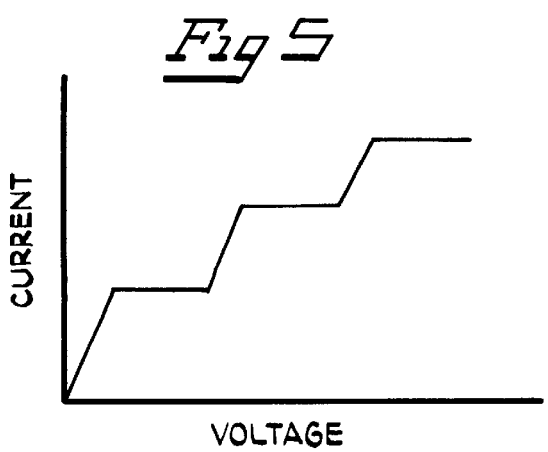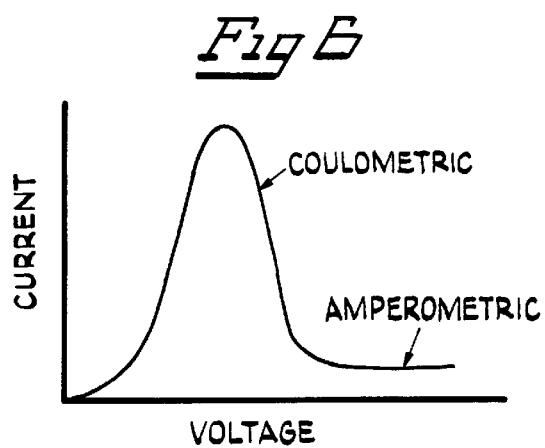

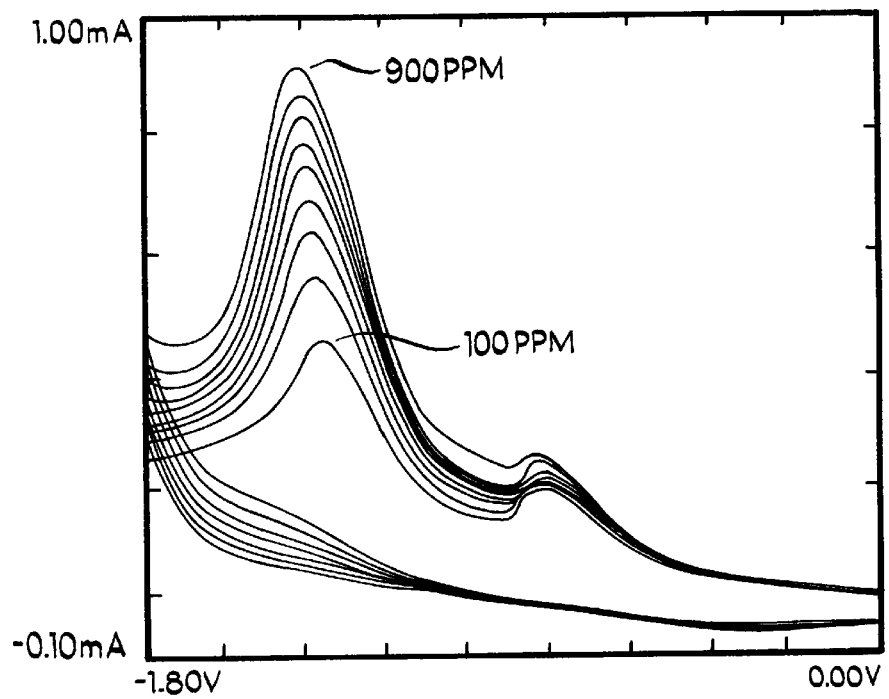
Fig 10  RESPONSE OF NOₓ SENSOR IN DIFFERENT CONCENTRATIONS OF NOₓ WITH 1% O2 SWEEP RATE 100mV/s, AT 500C
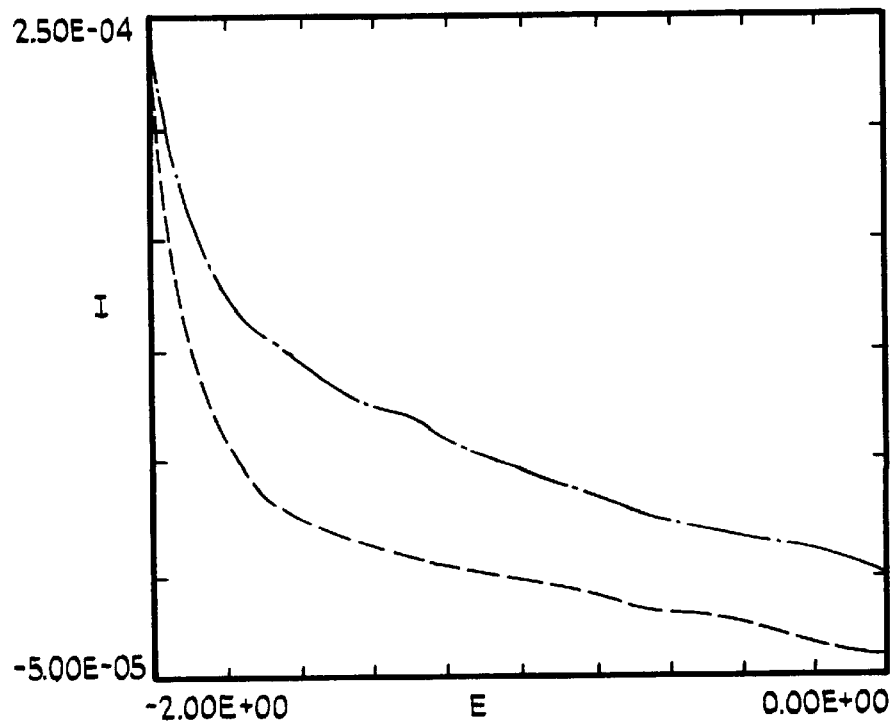
Fig 15  THE SENSOR RESPONSE IN 1000PPM N2O GAS AT WORKING TEMPERATURE 500C SCHEMATIC OF NOx SENSOR EFFECT OF SO2 ON NOx SENSOR PERFORMANCE 800 PPM NOx + 1% O2

800 PPM NOx + 1% O2 + 50 PPM SO2

800 PPM NOx + 1% O2 + 100 PPM SO2

THE RESPONSE OF NOx SENSOR TO NO2
AT WORKING TEMPERATURE 500C

THE RESPONSE OF NO$_x$ SENSOR TO NO
AT WORKING TEMPERATURE 500C

+N2

EFFECT OF INTERFERING GASES
WITH 500 PPM NO AND 1% O2

+200 PPM CO

+200 PPM CH4

+5% CO2

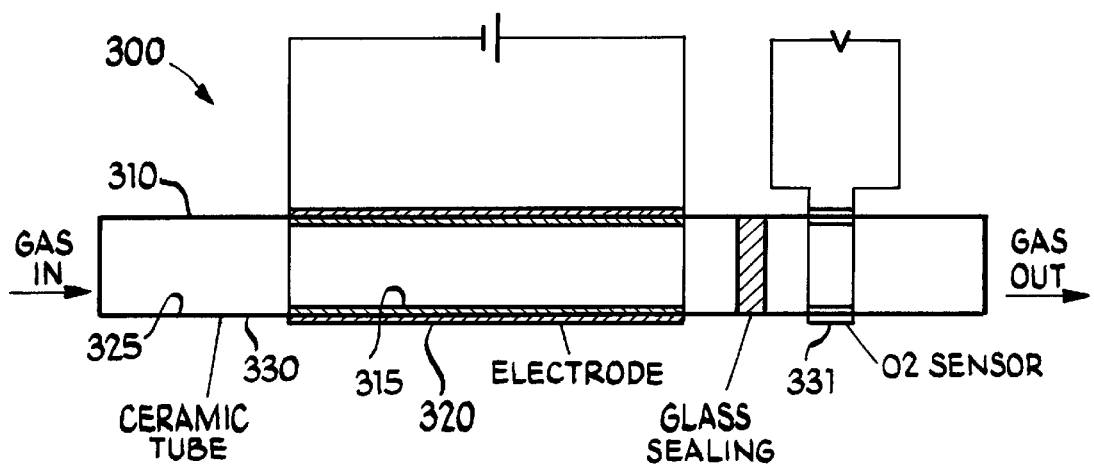
*Fig 19* A SCHEMATIC OF OXYGEN REMOVER
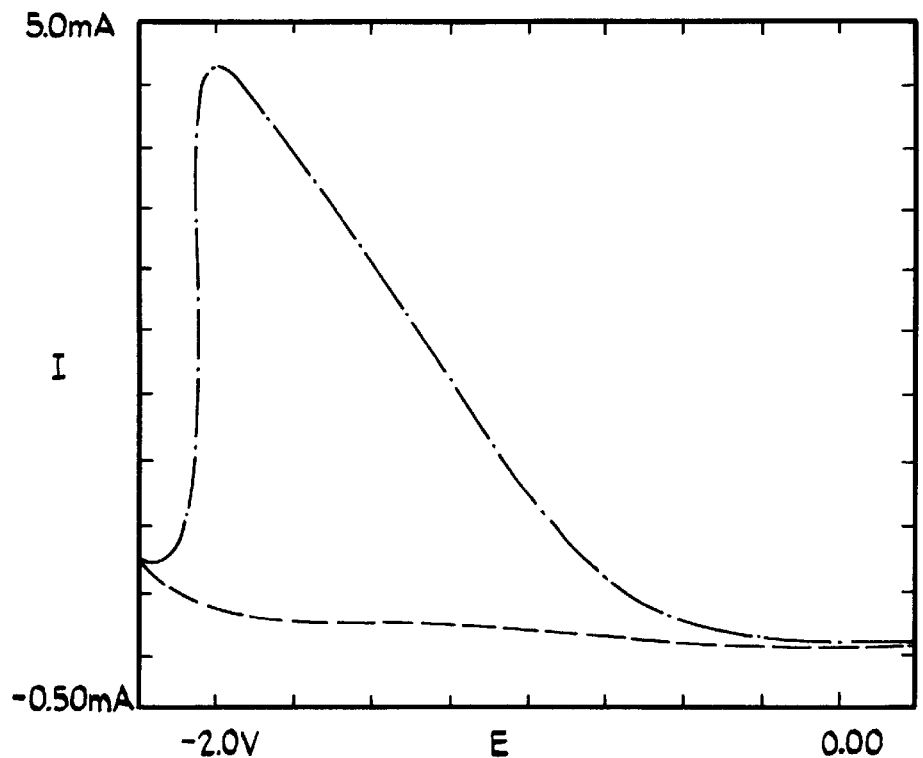
*Fig 20* SENSOR RESPONSE TO 500PPM NO IN 15% O2 WITHOUT AN OXYGEN REMOVER

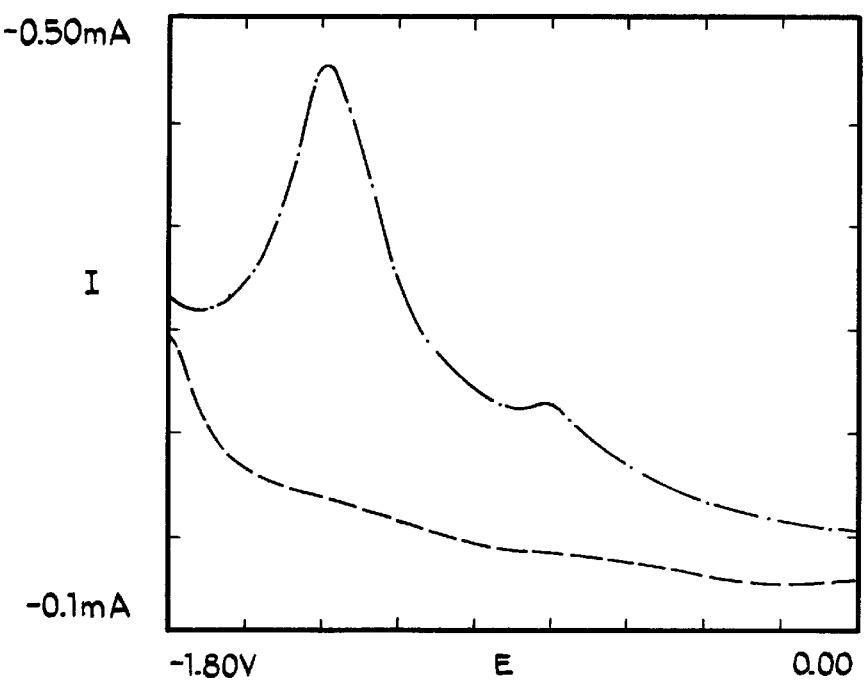
Fig 21 SENSOR RESPONSE TO 500PPM NO IN 15% O2 WITH AN OXYGEN REMOVER
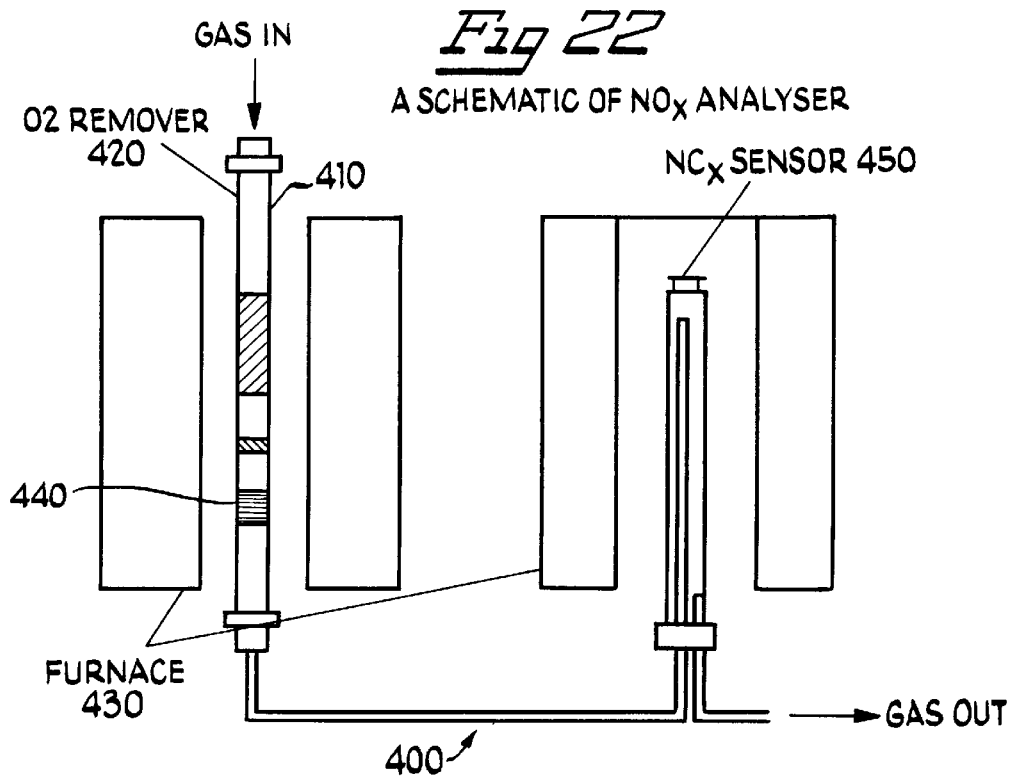
Fig 22 A SCHEMATIC OF NOx ANALYSER

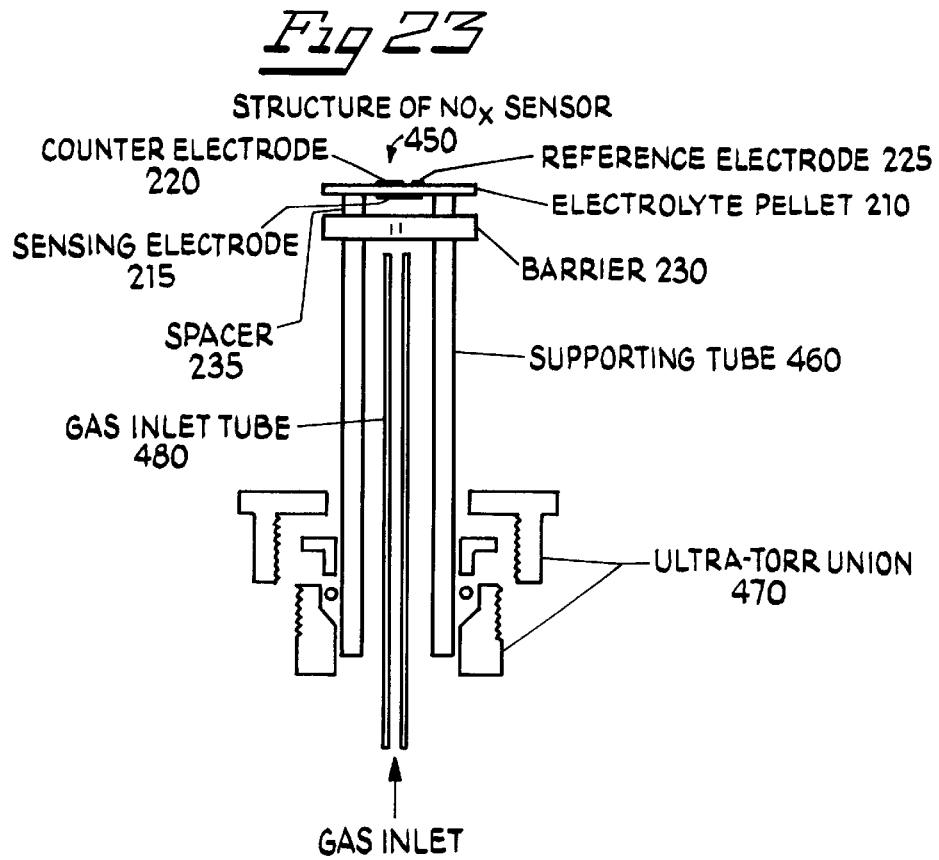
Fig 23
STRUCTURE OF NO$_x$ SENSOR
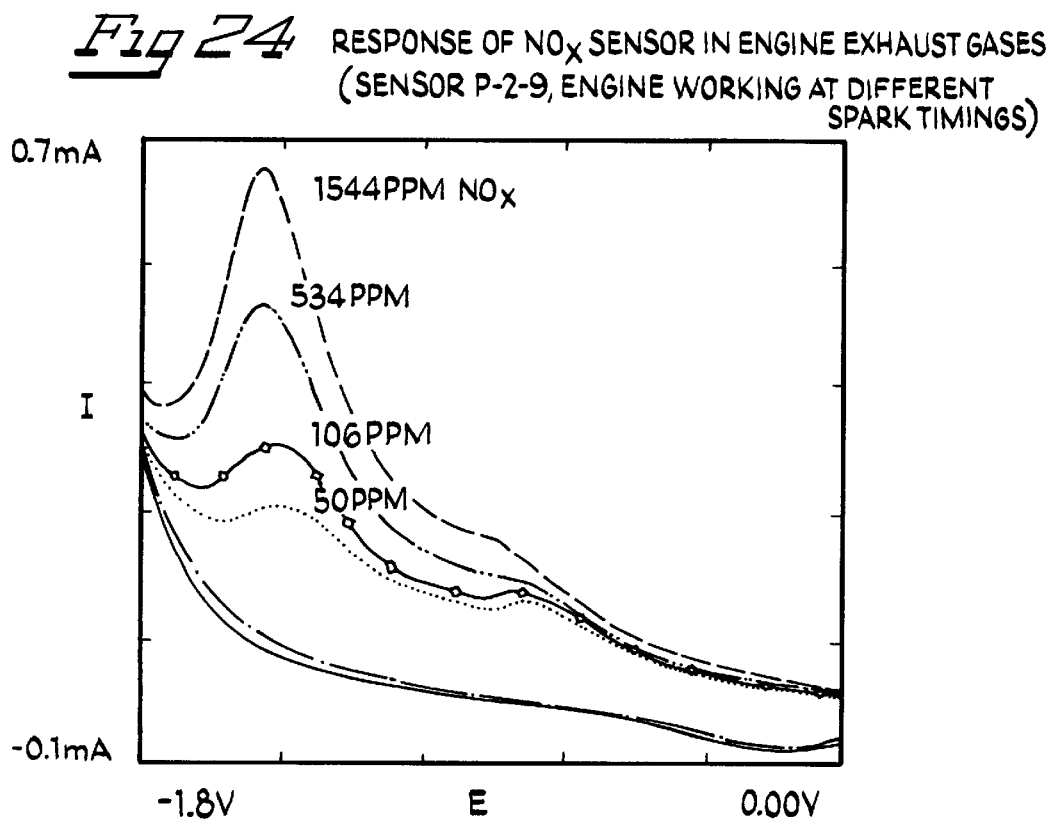
Fig 24 RESPONSE OF NO$_x$ SENSOR IN ENGINE EXHAUST GASES (SENSOR P-2-9, ENGINE WORKING AT DIFFERENT SPARK TIMINGS)

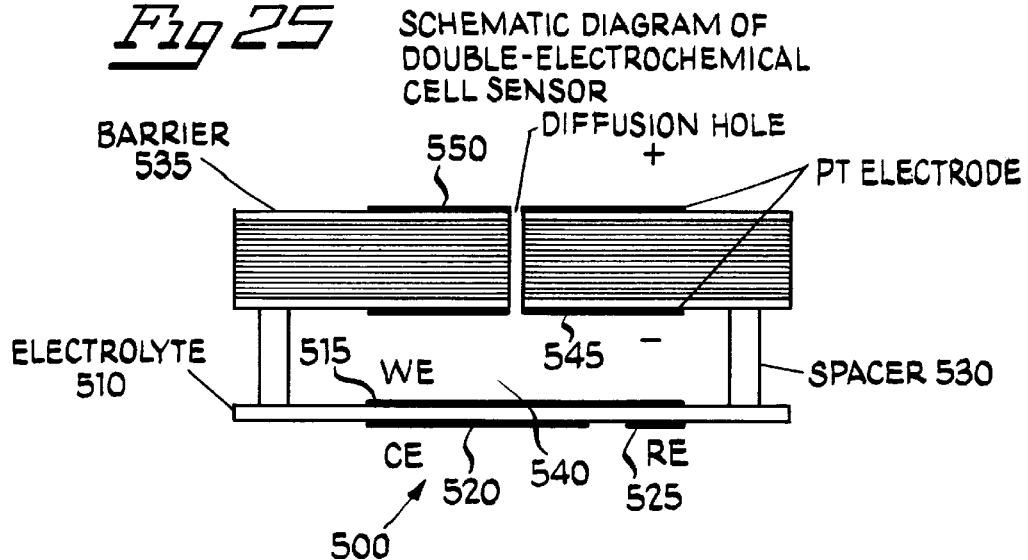
Fig 25. SCHEMATIC DIAGRAM OF DOUBLE-ELECTROCHEMICAL CELL SENSOR
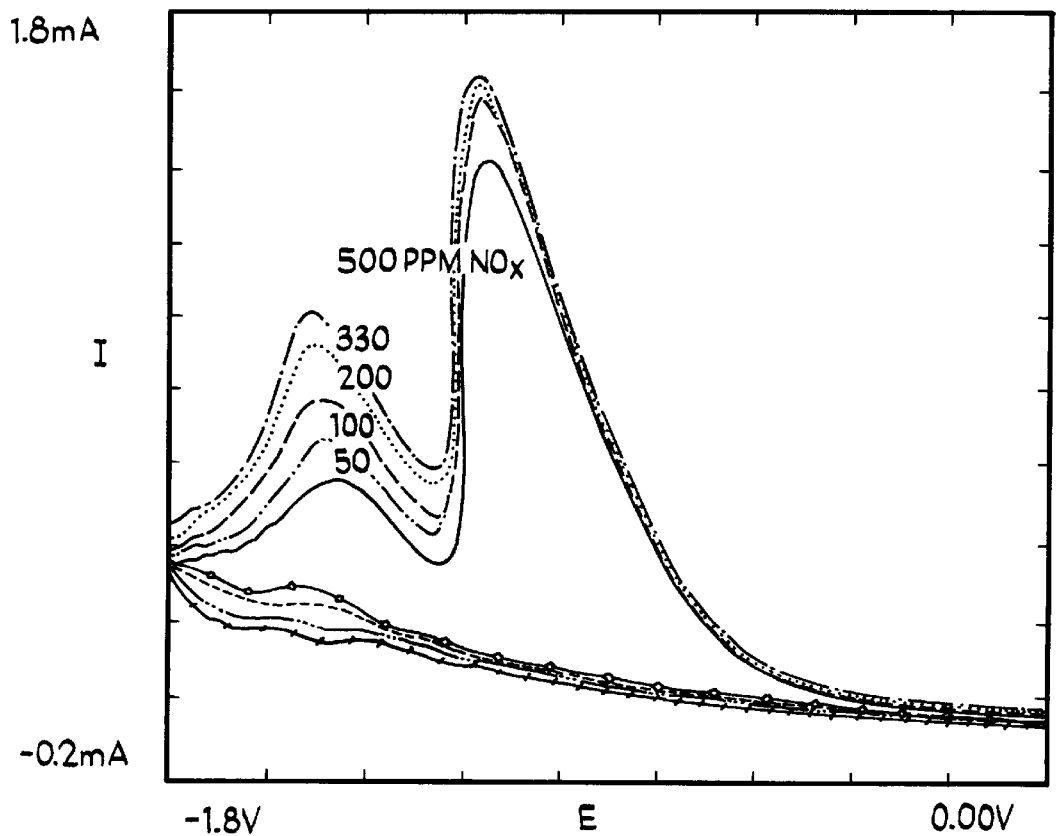
Fig 26. SENSOR RESPONSE TO $NO_x$ IN 15% $O_2$ WITH $O_2$ PUMPING WORKING AT -1.3V, 500C ns.
MULTI-FUNCTIONAL AND NO$_X$ SENSOR FOR COMBUSTION SYSTEMS This is a continuation-in-part of Ser. No. 08/482,958, filed Jun. 15, 1995, now U.S. Pat. No. 5,667,652, which is a file wrapper continuing application of Ser. No. 08/164,143, filed Dec. 9, 1993, now abandoned, which claimed priority under 35 U.S.C. §119 of PCT application PCT/US93/11274, filed Nov. 19, 1993. Priority of the filing date of the underlying PCT application is hereby claimed, under 35 U.S.C. §119 and §120. Priority is additionally claimed, under 35 U.S.C. §119(e) for the filing dates of provisional applications Ser. No. 60/012,659, filed Mar. 1, 1996 and Ser. No. 60/014,627, filed Mar. 6, 1996, from which provisional applications this application likewise depends.

BACKGROUND OF THE INVENTION

1. Field of the Invention

The subject matter of pending application Ser. No. 08/482,958, filed Jun. 15, 1995, is incorporated herein by reference. The invention relates to sensors for sensing gaseous components in the exhaust stream of combustion systems, and more particularly to multi-functional sensors for combustion control systems for selective and simultaneous sensing of more than one gaseous component in the exhaust stream from a combustion system.

2. The Prior Art

Combustion systems convert potential chemical energy in fuels (e.g. natural gas, other hydrocarbons, or hydrogen) into another form of energy such as heat or kinetic energy. The fuel is mixed with air or oxygen and combusted, whereupon the combustion products and unburned fuel and air are exhausted from the system in a gaseous stream. Well-known combustion systems include a wide variety of devices including boilers, furnaces, and reciprocating engines.

Both the efficiency and performance of a combustion system can be improved by regulation of the combustion process. For example, a precise control of the fuel to air ratio can significantly reduce fuel consumption, while simultaneously reducing toxic emissions in the exhaust stream. Regulation is typically accomplished by a control system that monitors the concentration of combustion products such as nitrogen oxides (NO$_X$), carbon monoxide (CO), unburned fuel and oxygen in the exhaust stream. The relative concentrations of these exhaust components provide information regarding the operation of the combustion system. Important operating parameters such as the fuel to air ratio may then be adjusted to improve operation of the combustion system. Although the requirements of control systems are specific for each different combustion process, the principles governing the control mechanism are similar.

Several problems exist with regard to the current sensing technology used in combustion control systems. Most existing sensors are capable of monitoring only a single exhaust gas component at a time in a combustion process. This component, typically O$_2$, is continuously monitored and the concentrations of other components are estimated based on mass balance of thermodynamic equilibrium calculations. However, combustion is a highly nonequilibrium process. Thus, concentrations determined in this manner may be quite inaccurate. Potentiometric sensing of other combustion product gases such as NO$_X$, SO$_X$, CO$_X$, and H$_2$S, and unspent fuel gases such as CH$_4$ and C$_3$H$_8$, have been reported but the sensors have demonstrated limited performance. Control systems could be significantly improved if several gaseous components could be accurately monitored, simultaneously.

Several ex-situ techniques based on optical phenomena are capable of multifunctionality, but suffer from other disadvantages. For example Fourier Transform Infrared (FTIR), and Non-Dispersive Infrared (NDIR) sensors can accurately monitor multiple gas concentrations, but are very large and expensive. Further, these sensors require the installation of gas sampling lines which makes the sensors even more cumbersome, and significantly delays control system response. As a result, these techniques are unsuitable for on-line detection, monitoring, and control of combustion systems with a feed back arrangement. Other ex-situ techniques such as Gas Chromatography (GC), Mass Spectrometry (MS), and most traditional chemical analysis methods are less expensive but are also equally cumbersome and time consuming. As such, these are not easily amenable to applications involving on-line detection, monitoring, and control. For these reasons, ex-situ sensors based on FTIR, NDIR, GC, MS, and traditional chemical methods are impractical for combustion control systems.

A need exists for a simple, los-cost, multi-functional sensor capable of sensing more than one gas component simultaneously. The sensor should be reliable and accurate, and be able to withstand the harsh environment of the exhaust stream from an operating combustion system. It has further been known that in lean burning conditions, such as in an internal combustion engine, oxygen concentration in the exhaust gases can be approximately 10–15%. This oxygen concentration is 3–4 orders of magnitude higher than the concentration of nitrogen oxides in the same exhaust gases. Oxygen concentrations of such high magnitudes can affect the operation of sensors configured for the detection of nitrogen oxides.

Accordingly, it is desirable to provide a sensor for the detection of oxides of nitrogen, while operating in an environment of high oxygen concentration. The subject invention relates to such a multi-functional sensor.

This and other objects of the invention will become apparent in view of the present specification, claims and drawings.

SUMMARY OF THE INVENTION

The present invention is directed, in part, to a sensor apparatus for sensing gaseous oxides of nitrogen in an exhaust stream for a combustion system.

The sensor comprises a solid electrolyte member fabricated from an oxygen ion conducting material, the electrolyte member having two sides, a first of the two sides being exposed to the exhaust stream, and the second of the two sides being positioned away from, and in an isolated manner, relative to the exhaust stream. A sensing electrode is operably associated with the first side of the electrolyte member, and in contact with the exhaust stream. A catalyst material is operably disposed on the sensing electrode, and capable of catalyzing a reduction reaction of nitrogen oxide. A counter electrode is operably associated with the second side of the electrolyte member. An optional reference electrode is operably associated with the second side of the electrolyte member, the reference electrode being separated from direct electrical contact with the counter electrode. A diffusion barrier is operably disposed in direct overlying physical contact with the sensing electrode, the diffusion barrier being substantially impervious to the transport of gaseous nitrogen oxide and other gases therethrough with the exception of a small diffusion aperture, so as to substantially preclude uncontrolled contact between the exhaust stream and the sensing electrode. A diffusion aperture, of desired dimensions, extends through the diffusion barrier, from the exhaust stream to the sensing electrode, for permitting controlled access and contact of gaseous components form the exhaust stream to the sensing electrode. Means are provided for electrically connecting the sensing electrode and the counter electrode for enabling application of a known electrical potential difference across the sensing electrode and the counter electrode, and for enabling a current flux to flow between the sensing electrode and the counter electrode. In addition, means are also provided for substantially removing oxygen from the exhaust stream operably disposed in a gas transporting relationship between the exhaust stream and the diffusion barrier.

In a preferred embodiment of the invention, the means for substantially removing oxygen comprises a tubular solid electrolyte member, operably disposed such that gases in the exhaust stream are constrained to travel through the tubular member in order to arrive at the sensing electrode, the tubular solid electrolyte member being operably configured from an oxygen ion conducting material, the tubular solid electrolyte member having an inner surface and an outer surface; a first remover electrode (cathode) operably associated with the inner surface of the tubular electrolyte member, and in fluid communication with the exhaust stream; a second remover electrode (anode) operably associated with the outer surface of the tubular electrolyte member; means for electrically connecting the first and second remover electrodes; and means for applying an electric potential difference across the two electrodes with the first remover electrode (cathode) at a lower electric potential such that upon application of the said electric potential difference, oxygen present in the tubular electrolyte member will be substantially driven outwardly from the interior of the tubular electrolyte member through the walls of the said electrolyte member.

In an alternative preferred embodiment of the invention, means for substantially removing oxygen from the exhaust stream, operably associated with the diffusion barrier are provided. The means for substantially removing oxygen comprises the diffusion barrier being fabricated for a material which is capable of permitting the transmission therethrough of oxygen ions; a first oxygen electrode disposed on a side of the diffusion barrier facing toward the sensing electrode; a catalyzing material disposed on the first electrode, capable of facilitating reduction of oxygen; a second oxygen electrode disposed on a side of the diffusion barrier facing away from the sensing electrode; means for applying an electric potential or voltage difference across the two electrodes such that the first oxygen electrode is at a lower (or negative) electric potential, whereupon the application of the voltage, oxygen present in the cavity between the diffusion barrier and the sensing electrode is caused to be reduced to oxygen ions and transported through the diffusion barrier away from the sensing electrode.

Alternative means for removing oxygen consisting of passing the exhaust gas through a tube containing fine copper metal turnings which serve to getter oxygen, prior to the exhaust gas coming into contact with the sensing electrode of the sensor. Copper turnings can be periodically regenerated by passing a reducing gas such as hydrogen.

In a preferred embodiment of the invention, the first and second oxygen electrodes are fabricated from a noble metal. Preferably, the noble metal is platinum. The material from which the diffusion barrier is fabricated includes at least one of the following materials: Yttria-stabilized zirconia (YSZ), doped ceria, certain perovskites, stabilized bismuth oxide.

The invention also comprises a method for sensing the concentration of a selected component, for example an oxide of nitrogen, in a gaseous mixture, comprising the steps of:

conducting an amount of a gaseous mixture to a sensor device, the sensor device including a solid electrolyte membrane fabricated from an ion conducting material, the electrolyte member having two sides, with a first side of the two sides being positionable toward the exhaust stream, and a second of the two sides being positionable away from and in an isolated manner relative to the exhaust stream;

a sensing electrode operably associated with the first side of the electrolyte membrane, and in fluid communication with the exhaust stream;

a catalyst material, operably disposed on the sensing electrode, and capable of catalyzing a reduction on the specific component of the gaseous mixture;

a counter electrode operably associated with the second side of the electrolyte membrane;

a diffusion barrier, operably disposed in direct overlying physical contact with the sensing electrode, the diffusion barrier being substantially impervious to the transport of the specific component of the gaseous mixture therethrough, so as to substantially preclude uncontrolled contact between the exhaust stream and the sensing electrode;

a diffusion aperture, having desired dimensions, extending through the diffusion barrier, from the exhaust stream to the sensing electrode, for permitting controlled access and contact of gaseous components form the exhaust stream to the sensing electrode;

electrical connections between the sensing electrode and the counter electrode for enabling application of a desired electrical potential difference across the sensing electrode and the counter electrode;

electrical connections between the sensing electrode and the counter electrode, for enabling a current flux to flow between the sensing electrode and the counter electrode;

applying an electrical potential across the sensing electrode and the counter electrode;

exposing the sensing electrode to the gaseous mixture;

catalyzing the specific component on the sensing electrode;

monitoring the current in the electrical connection between the sensing electrode and the counter electrode;

integrating the current plot which has been established as a result of the monitoring, the result of which integration is a numerical value which is proportional to the concentration of the specific component of the gaseous mixture.

The step of applying a voltage potential further comprises the step of applying a sweeping voltage.

The method further comprises the step of:

removing molecular oxygen from the gaseous mixture, prior to exposure of the sensing electrode to the gaseous mixture.

BRIEF DESCRIPTION OF THE DRAWINGS

FIG. 3 shows schematic current vs. voltage traces of a multi-functional coulometric sensor wherein the signal represents emptying (converting) of the various active gases contained in the volume of the cavity.

FIG. 4 shows schematic current vs. voltage traces of a multi-functional coulometric sensor wherein the signal represents emptying (converting) of the various active gases adsorbed on the surface of the catalysts in the cavity.

FIG. 5 is a schematic of the response of the multi-functional sensor for the detection and measurement of a number of gases in an amperometric mode.

FIG. 6 shows a coulometric signal of $NO_X$ gas under triangular voltage sweep, and a comparison between the coulometric and amperometric signals.

FIG. 10 is a current vs. voltage trace for linearly ramped voltage at 100 mV/sec for a gas mixture containing various concentrations of $NO_X$ in nitrogen.

FIG. 15 is current vs. voltage response of a prototype $NO_X$ sensor for a gas mixture containing 1000 ppm of $N_2O$ and balance nitrogen.

FIG. 19 is a schematic illustration of an oxygen remover according to an alternative embodiment of the present invention.

FIG. 20 is current vs. voltage response of a $NO_X$ sensor to 500 ppm of NO in 15% $O_2$ without pumping.

FIG. 21 is current vs. voltage response of a $NO_X$ sensor to 500 ppm of NO in 15% $O_2$ with an oxygen remover which essentially depletes the gas mixture of $O_2$ prior to its coming in contact with the sensing electrode.

FIG. 22 is schematic of a $NO_X$ analyzer with an in-line oxygen remover.

FIG. 23 is a more detailed schematic of $NO_X$ sensor which may be utilized in the analyzer of FIG. 22.

FIG. 24 is current vs. voltage response of $NO_X$ sensor to engine exhaust gas at various concentrations of NO.

FIG. 25 is a schematic of a $NO_X$ sensor according to an alternative embodiment of the invention, having an in-situ oxygen remover.

FIG. 26 is current vs. voltage response of the sensor shown in FIG. 25 wherein the oxygen remover is built-in onto the body of the sensor.

BEST MODE FOR CARRYING OUT THE INVENTION

Figure 1:
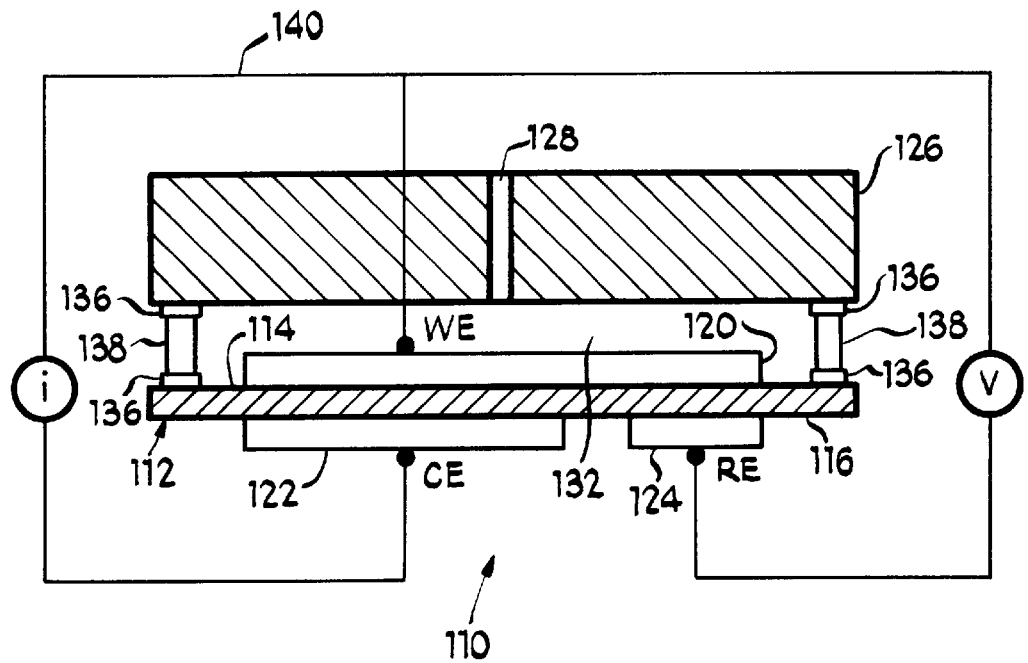
FIG. 1 is a schematic drawing of a multi-functional sensor based on coulometric principles for use in a control system for natural gas combustion systems.

While this invention is susceptible to embodiment in many different forms, there is shown in the drawings and will be described herein detail, several specific embodiments, with the understanding that the present invention is to be considered as an exemplification of the principles of the invention, and is not intended to limit the invention to the embodiments illustrated.

The invention includes a multi-functional sensor which can simultaneously sense more than one gas component in a combustion system's exhaust stream. The sensor is based on electrochemical principles which permit simplicity and low-cost in both construction and operation. Further, the sensor uses an ion-conducting solid oxide electrolyte material, which is particularly suitable for use in the harsh environment in the exhaust stream of, for example, a natural gas combustion system. The sensor provides increased flexibility during operation since it is operable in either a coulometric or an amperometric mode. The principal focus of the sensor will be coulometric operation since the signal strength is considerably greater in this mode which leads to enhanced sensitivity over the amperometric mode of operation.

The sensor includes a solid oxide ion-conductive electrolyte membrane having a first surface proximal to the exhaust gases of a combustion system, and a second surface isolated from the exhaust gases. (It is to be noted, however, that the sensor operating principle does not preclude its operation in such a manner that both surfaces are exposed to the same exhaust gas.) The first surface of the membrane is associated with (e.g. adhered to, deposited on, fired upon, grown upon, etc.) a sensing electrode including finely divided catalyst material capable of catalyzing the electrochemical reduction or oxidation of at least one gaseous component from the exhaust gas stream. The sensing electrode may in turn be coated with a porous diffusion barrier to limit diffusion of certain components in the exhaust stream to the electrode surface. The second surface of the electrolyte membrane is associated with a counter-electrode including a finely divided catalyst material suitable for catalyzing electrochemical oxidation or reduction of the chemical species electrochemically oxidized or reduced at the sensing electrode. Optionally, a reference electrode may be associated with the second surface proximal to the counter-electrode. FIG. 1 is a schematic drawing of the multi-functional sensor of the present invention.

The ion-conductive electrolyte membrane is permeable only to a specific chemical species. For example, in a sensor for use with oxygen-containing gases ($NO_X$, $SO_X$, $CO_X$, $O_2$, etc.), the electrolyte membrane is permeable only to oxygen ions. In a sensor for use with hydrogen containing gases ($CH_4$, $H_2S$, etc.), the electrolyte membrane is permeable only to protons.

It is the electrode material, however, that provides a multi-functional sensing operation. Different electrode materials, each highly selective to a gaseous component, may be integrated onto a single electrolyte material. In this manner, sensors highly selective to specific gaseous components may be constructed.

In operation, for example in a sensor for use with oxygen-containing gases, exhaust gases from a natural gas combustion system are allowed to contact the sensing ("working") electrode surface. A negative (lower) potential is applied to the sensing electrode to facilitate electrochemical reduction of at least one oxygen-containing gaseous component of the exhaust stream. When a negative (lower) potential sufficient to reduce a gaseous oxide to be sensed is applied to the sensing electrode (the cathode) with respect to the counter electrode (optionally contained within an enclosed air atmosphere), the gaseous oxide is reduced. The oxygen ions are then conducted through the ion-conductive electrolyte membrane to the counter electrode (the anode) where they oxidize to oxygen molecules. Electrons involved in the reaction flow from the anode to the cathode through an external electrical connection (e.g. wire) enabling measurement of an electrical current which is a function of the concentration of the chemical species involved. In an exhaust stream, each thermodynamically stable gaseous oxide couple (e.g. $SO_2/SO_3$, $S_2/SO_2$, $CO/Co2$) usually has a characteristic reduction potential which depends mildly on the concentrations of the species. In cases such as $NO_X/N_2$, the characteristic reduction potential is kinetic since $NO_X$ is thermodynamically unstable; but it is stable kinetically. Thus, the catalyst has a profound influence on the effectiveness of the approach. It is these characteristic redox couples and their ranges, whether they be thermodynamic or kinetic, enable different redox couples to be readily distinguished from other components in the exhaust stream.

Under the application of a voltage which linearly increases with time up to certain voltage followed by a subsequent decrease to zero voltage, typical of linear sweep cyclic voltammetry, current peaks will occur at discrete characteristic potentials associated with certain oxide pairs. It is to be noted, however, that the sensor response is not voltammetric, rather it is coulometric as the signal is governed not by diffusion but by the size of the cavity or by the size of the sensing electrode. In a multi-component system having multiple sensing electrodes on a single electrolyte membrane, with each electrode highly sensitive to a specific gaseous component, the areas under individual peaks are proportional to the concentrations of the respective species in the working gas (exhaust stream).

A given species can be distinguished by the characteristic electric potential at which a peak is observed. The preceding assumes that the peaks due to different species are sufficiently separated from each other and not overlapping. The concentration of a given species can be estimated from the area of under the requisite peak, less the background. With 1 as the current and V=Et as the applied (instantaneous voltage), the area under a given peak is given by $$\text{PeakArea} = \int I dV = E \int I dt = EQ \tag{1}$$

where Q is the net charge transported through the ion conducting electrolyte. The following discussions given with the assumption that electrolyte is an oxygen ion conducting material. It is to be emphasized, however, that the approach is entirely general and can be adapted to other species by making appropriate changes in the constants. The following also assumes that there is no charging current effects (e.g. capacitive). The number of $O_2$ molecules pumped out is given by $$\frac{QN_A}{4F} = \frac{N_A \int I dV}{4FE} \tag{2}$$

where, $N_A$ is Avogadro's number. The number of $O_2$ molecules pumped out directly gives information on the concentration of the particular oxygen containing gaseous species under consideration. The size of the signal depends upon the geometric aspects of the sensor design, in particular the cavity volume, V. As an illustration, consider that the gas in question has a stoichiometry of $GO_X$, where G is a nonmetal whose oxide is to be sensed. Then, the number of moles of $GO_X$ present in the cavity is given by $$n_{GO_X} = \frac{Q}{4 \times F} = \frac{\int I dV}{4 \times FE} \tag{3}$$

and the partial pressure of the gas ($GO_X$) in the working gas is given by $$P_{GO_X} = \frac{n_{GO_X} RT}{V} = \frac{QRT}{4 \times FV} = \frac{RT \int I dV}{4 \times FEV} \tag{4}$$

Figure 2:
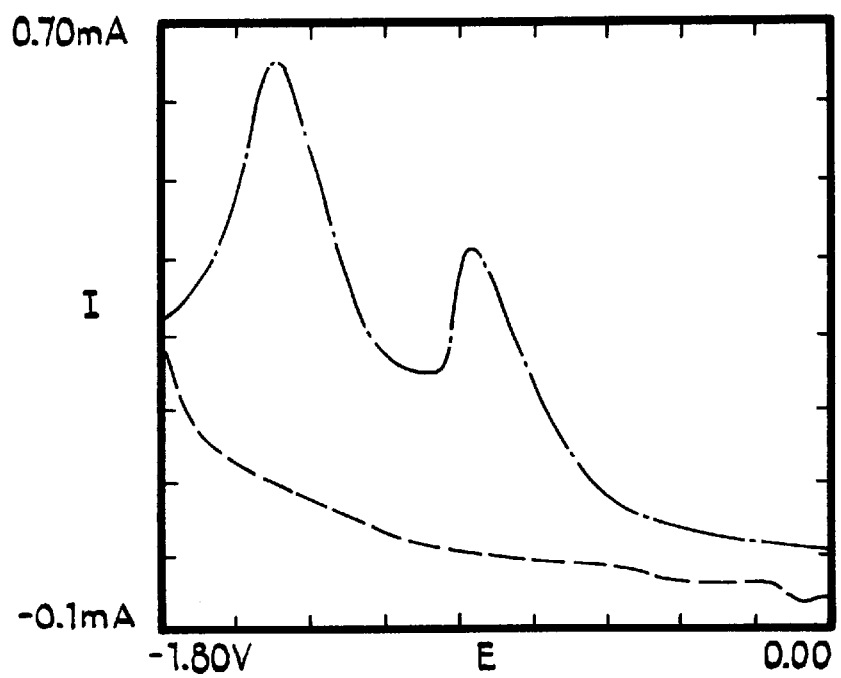
FIG. 2 shows an actual current vs. voltage trace of the multi-functional sensor of the present invention with $NO_x$ and oxygen as the two active species in addition to inert nitrogen.

The preceding assumes that selective adsorption of the species under consideration does not occur. Should this not be the case, the area under the peak will be related not only to the species in the cavity but also that adsorbed on the catalyst. In such a case, the size of the sensing electrode, the amount and specific area of the catalyst are important. This aspect can be taken into account via an appropriate calibration procedure. The multi-functional sensor with an oxygen ion conducting electrolyte can distinguish and measure concentrations of gases such as $O_2$, $NO_X$, $SO_X$, and the like. FIG. 2 shows an actual experimental trace of a gaseous mixture consisting of oxygen, $NO_X$, and an inert gas ($N_2$).

While the configuration of sensors for hydrogen-containing gases is similar to that for oxygen-containing gases, the electrolyte materials differ. Proton conductors are employed as solid electrolyte membranes for hydrogen-containing gases, and the sensing electrode (the anode) consists of finely divided particles of a catalyst such at Pt, Ni, etc. (for oxidation of $H_2$ or hydrocarbons). The correlation between the sensor response (integrated current vs. time response, i.e. charge in coulombs) and concentration of the species to be sensed is essentially the same as for oxygen, with the exception that the number of Faraday equivalents per mole of the species electrolyzed will be dependent upon the valence of the electroactive species transported through the electrolyte. The peaks in the current vs. voltage trace occur at different positions (voltages) and integrated areas are coulometric signals for the respective species as shown schematically in FIG. 3. The sizes (height and area) of the peaks depend upon the volume of the cavity.

In a multi-function sensor having more than one sensing electrode on an electrolyte membrane, a catalyst used for a particular species will exhibit specific adsorption affinity to that particular species and none other. In this manner, various catalysts collectively adsorb the various species that the multi-functional sensor of this invention senses. The expected current vs. voltage response under the application of a triangular sweep is of the type shown in FIG. 4. Sensor response here directly relates to the surface coverage, $\theta$. The size of the peaks depend upon the electrode size. This mode of operation is termed coulometric.

The multi-functional sensor of this invention also can operate in an amperometric mode. In this mode of operation, the current vs. voltage response is measured under steady state conditions for various values of the applied voltage. The expected response is shown in FIG. 5. However, the signal corresponding to a given concentration is lower than the coulometric mode of operation and it thus exhibits less sensitivity as compared to the sensor described in this invention. FIG. 6 compares the expected signal for a gas containing 500 ppm of NO in the coulometric mode of operation to that in the amperometric mode obtained through theoretical calculations. It has been found that the signal for the coulometric mode of operation is considerably (more than 100 times) that of the amperometric mode. The response time of the coulometric sensor is also expected to be lower (faster response) than the corresponding amperometric mode of operation. This is because, in the amperometric mode, it is necessary to establish the steady state at each of the applied voltage before the plateau regions can be established. By contrast, in the coulometric mode of operation, a continuous sweep essentially empties the cavity with respect to each of the requisite species in a sequential manner, once the critical voltage for the corresponding electrochemical reaction has been exceeded.

Figure 7:
FIG. 7 is a schematic drawing of a multi-functional sensor installed in fluid communication with the exhaust stream from a natural gas combustion system.

Referring to FIGS. 1 and 7, a multi-functional sensor 110 for a natural gas combustion system includes an ion-conductive electrolyte membrane 112 constructed from a ceramic solid oxide material. The specific composition of the electrolyte membrane may vary according to the requirements of particular applications. Electrolyte membrane 112 has a first surface 114 proximal to the exhaust stream from a natural gas combustion system, and an opposing second surface 116 isolated from the exhaust stream. A sensing electrode 120 adheres to at least a portion of the first surface 114 of the electrolyte membrane, and a counter-electrode 122 adheres to a portion of the second surface. The sensing electrode includes a porous layer of a catalytic material (e.g. a vanadia-based material) atop a substrate made of fine particles of a conductive material (e.g. palladium or platinum). The specific composition of both the sensing (120) and the counter (122) electrodes also may vary according to the requirements of particular applications.

The sensing electrode 120 may be covered by a diffusion barrier 126, either as a porous layer or a dense disc with a diffusion hole, which limits the amount of the exhaust gas that may diffuse to the sensing electrode. In a preferred embodiment, the diffusion barrier is constructed from the same material as the electrolyte membrane to eliminate complications from thermal expansion mismatches and to avoid chemical interactions. Alternatively, the diffusion barrier may be constructed from alumina, other ceramics of matching thermal expansion coefficients, as well as metallic materials of matching thermal expansion coefficients. A laser bored diffusion aperture 128, typically less than 120 microns ($\mu$m) in diameter, establishes fluid communication between the exhaust stream and the sensing electrode 120. Methods other than laser boring, such as fiber introduction during casting or green-forming, may also be used to create the diffusion aperture.

In a preferred embodiment best illustrated by FIG. 1, an exhaust gas compartment 132 in fluid communication with the exhaust stream is disposed between diffusion barrier 126 and the electrolyte membrane 112. Fluid access to the exhaust gas compartment may be achieved through diffusion aperture 128. The exhaust gas compartment allows exhaust gases entering through the diffusion aperture 128 to diffuse out and contact a larger area of the sensing electrode 120. Exhaust gas compartment 132 is sealed around its edges to the diffusion barrier 126 and the electrolyte membrane 112 by glass seals 136 at the ends of ceramic spacers 138. Thus, the atmosphere inside the exhaust gas compartment is limited to exhaust gases that diffuse in through the diffusion aperture.

Sensing electrode 120 and counter electrode 122 are electrically connected via electrical connection means 140 though a voltage source capable of applying a voltage potential difference indicated by reference letter V between the sensing electrode and the counter electrode. The electrical connection also enables an electrical current indicated by reference letter 'i' to flow between the sensing electrode and the counter electrode. Preferably, electrical connections are silver wires of 0.25 mm (0.01") in diameter, attached to the electrode connections as silver paste.

The resulting connections may be fired at 500° C. for 30 minutes to set-up the silver paste, and bond the electrical connection to the electrodes.

In a preferred installation configuration best illustrated in FIG. 7, the sensor 110 is mounted in the wall 144 of the exhaust pipe from a natural gas combustion system. Exhaust gases from the exhaust stream are in fluid communication with the diffusion barrier 126, and thus free to diffuse through the diffusion aperture 128 to the sensing electrode 120, while the counter electrode 122 is isolated from the exhaust stream in a separate air atmosphere. Such a configuration is, however, optional and the counter electrode may also be in fluid communication with the exhaust stream.

Figure 8:
FIG. 8 is a schematic drawing of a multi-functional sensor with multiple electrodes based on coulometric principles for use in a control system for natural gas combustion systems.

Referring now to FIG. 8, a multi-electrode embodiment having a plurality of different sensing electrodes $SE_1$–$SE_4$ is schematically illustrated. Each sensing electrode may be constructed from a material having a high selectivity for a specific component in the exhaust gas stream. High selectivity to a chemical species results from specific adsorption of the chemical species at a catalyst. For example, the catalysts used for $NO_X$ sensors strongly adsorb $NO_X$ at the electrode surface, whereas other gas components in the mixture exhibit little or no affinity towards this catalyst. In this manner, sensors highly selective to $NO_x$, CO, unburned hydrocarbons, and other combustion products, etc., can be constructed.

During operation, exhaust gases from the combustion system diffuse through diffusion aperture 128 into the exhaust gas compartment 132 where they contact the sensing electrode 120. In a sensor for oxygen containing gases ($NO_x$, $CO_2$, $O_2$, CO, etc.), a negative electric potential is applied to the sensing electrode 120 with respect to the counter electrode 122 which is exposed to air. In a sensor for hydrogen containing gases ($CH_4$, $H_2S$, and other hydrocarbons), a positive voltage is applied to the sensing electrode 120, which is exposed to a hydrogen-containing atmosphere, with respect to the counter electrode 122. The counter electrode 122 in both cases may be exposed to oxygen or may also be immersed in the same atmosphere as the sensing electrode.

In the case of a sensor for oxygen-containing gases operating under a linear voltage sweep, when negative potential sufficient to reduce an oxide to be sensed is applied to sensing electrode 120 (the cathode), the oxide is reduced, and the oxygen ions move through ion-conductive electrolyte membrane 112 to the counter electrode 122 (the anode) where the oxygen ions are oxidized to oxygen molecules in the exit (air) atmosphere. In the case of a sensor for hydrogen-containing gases operating under an applied linear voltage sweep, when a positive potential sufficient to oxidize hydrogen-containing chemical species to be sensed is applied to sensing electrode 120 (the anode in this case), the species is oxidized, and protons move through the electrolyte membrane to counter electrode 122 (the cathode in this case) where they are reduced to hydrogen molecules. Electrons involved in the redox reactions move from the anode to the cathode through electrical connection means 140 enabling measurement of an electrical current, the magnitude of which is proportional to concentration of the chemical species involved in the redox reaction. More precisely, the integrated current-time trace (charge in coulombs) is proportional to the concentration of the chemical species involved in the redox reaction. In each of the above cases, the signal is the net charge transported under the linear (or triangular) sweep applied; that is the signal is coulometric.

For a multi-component system, the anticipated signal for a given species will occur above the appropriate critical voltage, and the integrated peak area (charge), which is a measure of its concentration, will be distinct as shown in FIG. 3. This represents the case wherein the signal is related to the amount of the species in the cavity, wherein the peaks drop off abruptly. However, if the catalyst exhibits affinity to the specific species so that it is chemisorbed, the signals will appear as shown in FIG. 4 in which the signal is nearly Gaussian.

Figure 9:
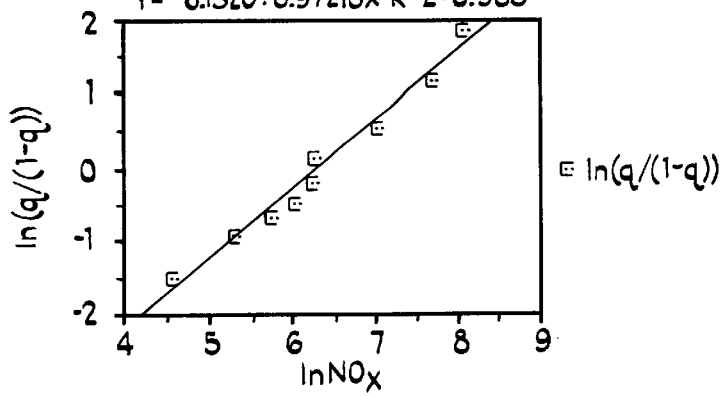
FIG. 9 shows a plot of the natural logarithm of surface coverage, $\theta$ plotted as $\ln(\theta/(1-\theta))$ vs. $\ln P$ for NO.

In the case of a multi-functional sensor having a plurality of different sensing electrodes such as illustrated in FIG. 8, each electrode has a high selectivity for a specific gas component in the exhaust stream, and not to any other. This high selectivity may be in the form of a greater adsorption affinity or a lower overpotential for decomposition, or both. The electrode kinetics can significantly shift the required electric potential for redox reactions from the thermodynamic value. This potential shift in principle can be tailored by means of electrocatalysis to detect each gas component in the exhaust stream selectively. The high selectivity to a chemical species stems from the specific adsorption of the species on the catalyst, or due to the relative ease of electron transfer. Thus, the sensor response is directly related to the volume of the cavity if the role of the catalyst is to reduce the overpotential without much adsorption (FIG. 3) in which case the current abruptly drops after the peak, or is directly related to the surface coverage if the catalyst exhibits high selectivity to adsorption (FIG. 4) in which case the individual current peaks are more Gaussian and the current does not abruptly decrease after the peak. In the latter case, the surface coverage may be related to the concentration of the specific gas via one of the suitable adsorption isotherms such as Langmuir adsorption isotherm. FIG. 9 shows experimentally estimated behavior for $NO_x$.

The composition of both ion-conductive electrolyte and electrode materials may be varied according to the requirements of particular applications. In principle, any suitable oxygen anion conductors can be used for oxygen-containing gases, and, any suitable proton conductors can be used as electrolyte for hydrogen-containing gases.

It is required, however, that the electrolyte be stable in the atmospheres it is to be used, and under the application of the required voltage. For oxygen and oxygen-containing gases, zirconia-based ceramics such as tape-case or isostatically pressed and sintered yttria-stabilized zirconia (YSZ) with a thickness typically less than 0.2 mm, and thoria-based ceramics are suitable electrolyte materials for the coulometric sensor described here. For hydrogen and hydrogen-containing gases, proton conductors such as trivalent rare earth oxide doped $BaCeO_3$ and $SrCeO_3$ are suitable electrolyte materials. Electrode materials suitable for oxygen-containing gases include noble metals (Pt, Pd, Ag, Au, etc.), perovskites (Sr-doped $LaMnO_3$ or LSM, Sr-doped $LaCoO_3$ or LSCo, and other oxide perovskites containing transition metals), other mixed conducting oxides, transition metal sulfides, and mixtures of them. Electrode materials suitable for reduction of $NO_x$, $SO_x$, $CO_x$, $H_2O$, as well as for oxidation of $H_2$, $CH_4$, and other unburned hydrocarbons include alumina support-iron based catalysts, vanadia-based catalysts ($V_2O_5/TiO_2$, $V_2O_5/Al_2O_3$, $V_2O_5/SiO_2$, etc.), nickel-based catalysts, and mixtures thereof. $V_2O_5$-based catalysts containing 50% of solid (balance porosity), which consists of 10 mol. % of $V_2O_5$ and 90 mol. % $TiO_2$ are suitable catalysts for sensors for the detection and measurement of $NO_x$ in $O_2$-containing atmospheres.

The subject invention is further explained by the following illustrative examples. The examples are given to explain the present invention. It is understood that the examples do not limit the scope of the present invention, but merely serve to explain the invention.

EXAMPLE 1

Several batches of coulometric sensors were fabricated as per the schematic shown in FIG. 1, having diffusion barriers made in different ways (laser-drilling after sintering or introduction of a polymeric fiber during pressing which can be subsequently burnt off to form a hole) of varying diameters (from about 10 $\mu$m to about 140 $\mu$m). Several current vs. voltage traces for gas mixtures containing oxygen and nitrogen oxides are shown in FIG. 10 in which the oxygen concentration was 1%. The temperature was 450° C. and the sweep rate was 100 mV/sec. The maximum applied voltage was 1.8 volts corresponding to a cycle period of 36 seconds. The abrupt drop in the current after the peak is indicative of emptying of the cavity. Thus, in this case, the integrated peak is representative of oxygen in the cavity and there is little, if any, oxygen adsorption contributing to the overall signal. The actual procedure for sensor testing is given in what follows.

Fabricated sensors were positioned in a ceramic tube which was placed in a tubular furnace controlled at a constant temperature. Pre-mixed sample gases were allowed to flow through the ceramic tube at a controlled flow rate, typically from 60 to 150 ml/min. Each and every gaseous component in the feed mixture is individually adjustable and controllable using the equipment.

A potentiostat/galvanostat (EG&G PAR 273) interfaced with a computer (IBM 286) was used to sweep the potential and to collect the current response of sensor undergoing tests. The current vs. voltage traces displayed on the computer screen after each potential sweep, and were printed to obtain a hard copy (such as FIG. 10). FIG. 10 shows current vs. voltage traces for various concentrations of $NO_X$ in the feed gas.

Figure 11:
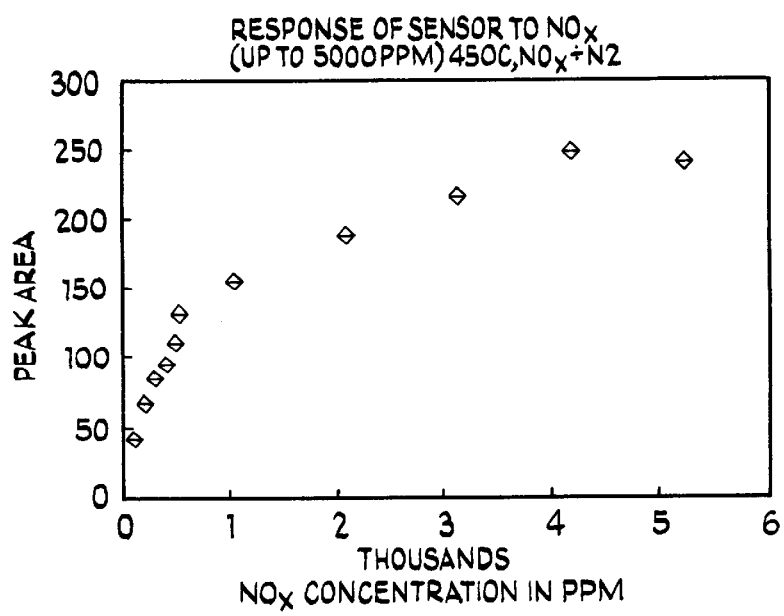
FIG. 11 is a plot of the $NO_X$ peak area vs. concentration.

FIG. 11 shows peak area vs. $NO_X$ concentration. Note that the peak area seems to saturate at high $NO_X$ concentrations. This behavior is consistent with adsorption of $NO_X$ on the surface of the catalyst. A test of the possible surface adsorption according to Langmuir adsorption isotherm is that the plot of $\ln(\theta/(1-\theta))$ vs. $\ln p$ where $\theta$ denotes the fraction of surface sites adsorbed should be linear with slope equal to 1.0. Defining $\theta$—(Peak area/Saturation peak area), the data shown in FIG. 11 are plotted in FIG. 9 shown previously. Note that the plot is a straight line with a slope of 0.97 (close to 1.0). This plot can be used as a calibration curve for the estimation of $NO_X$ concentration in a given gas mixture from the measured peak area.

EXAMPLE 2

Effect of Other Gas Species

Figure 12:
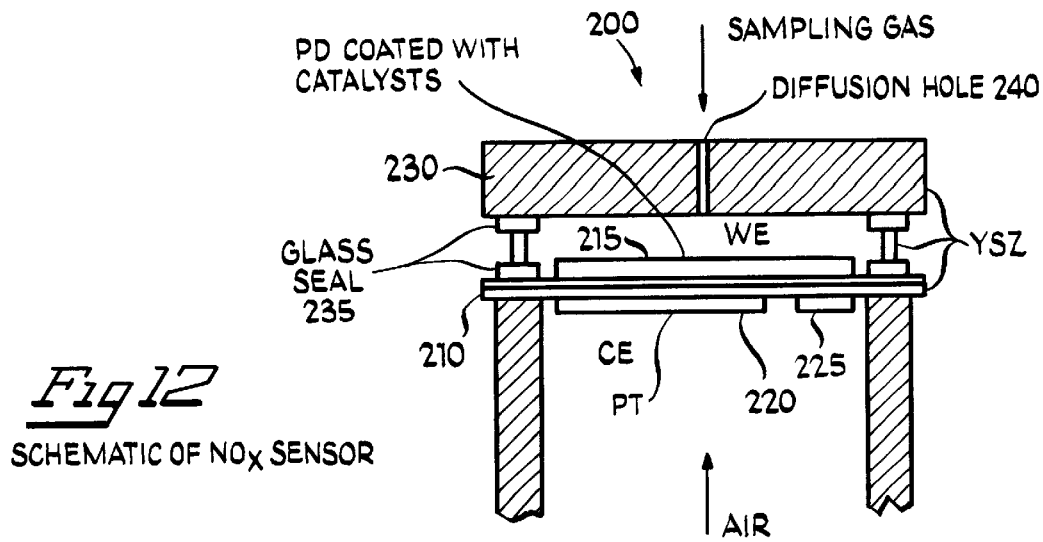
FIG. 12 is a schematic illustration of a further embodiment of the $NO_X$ sensor according to the present invention.

The present invention also includes a nitrogen oxide sensor which can sense nitric oxide and nitrogen dioxide in a complex i.c. engine exhaust gas environment. This will be detailed in a series of figures in what follows. The sensor, schematically illustrated in FIG. 12, is based on a ceramic electrolyte and a catalytic sensing electrode. Sensor 200 is fabricated from a tape-cast and sintered electrolyte pellet 210, on which the sensing electrode 215, and counter electrode 220 are formed, such as by screen-printing. Sensor 200 will be situated in an exhaust gas stream such that sensing electrode 215 "faces" the exhaust stream. A diffusion barrier 230 is provided, which is affixed to sensing electrode 215 by a glass-type seal 235. Seal 235 extends around the periphery of the sensing electrode 215, so as to preclude access to the sensing electrode 215. Aperture 240, which has a diameter on the order of few to several tens or even hundreds of micrometers ($\mu$m), is provided in diffusion barrier 230, to permit sensing electrode 215 to be exposed to the gas to be sampled. The counter electrode is exposed to an ambient air atmosphere.

During operation, sensor 200 is heated, such as by a gas furnace heater or an electrical resistance heater, to working temperature (approximately 350 to 500° C.), and linearly sweeping cathodic voltage is applied to the sensing electrode 215 versus the counter electrode 220. The sensor given in FIG. 12 is contemplated as being operated in a voltammetric mode, i.e. under a triangular sweep. It is to be understood, however, that the sensor response is not typical of a voltammetric response; rather, it is a coulometric response.

The current between the sensing electrode 215 and the counter electrode 220 is recorded. At a sufficiently fast sweep rate, isolated current peaks, one each corresponding to various active gaseous species will be obtained. The magnitude of the given peak (area)—less the background, is an accurate measure of the concentration of the species in the gas mixture which is sampled.

The sensing electrode 215 is fabricated of two layers. The base electrode layer will preferably be coated directly onto the electrolyte pellet 210. The base electrode layer may be fabricated from a noble metal such as platinum, palladium or gold, or a perovskite material such as LSM, LSCo, or many other oxide perovskites containing transition elements.

On the surface of the base electrode material, a coating of a catalytic material is applied wherein the catalytic material is capable of catalyzing the electrochemical reduction of nitrogen oxides, but little or no activity for the catalyzation of other gas species. Accordingly, the present invention is directed to an improved gas sensing electrode, using various electrode materials and manufacturing processes, which enhances the sensitivity of the sensor to $NO_X$, while at the same time suppressing the reduction of oxygen and other gas species such as CO, $CH_4$, and $CO_2$, improving the selectivity of the sensor.

Since the concentration of oxygen in an i.c. engine exhaust can be as high as 15%, several methods have been considered for enabling the measurement of ppm levels of $NO_X$ concentrations, which are several orders of magnitude smaller than the accompanying oxygen concentration. One such method involves the placement of an oxygen remover in the gas stream which is being directed to the sensor, so as to remove the majority of the oxygen in the gas stream before the stream reaches the sensor. The present invention involves, in one particular embodiment, the incorporation of an oxygen remover. Another method of improving the sensitivity for $NO_X$ in exhaust gases containing high concentrations of oxygen is to maintain a relatively low concentration of oxygen in the sensing cavity itself, by constantly pumping oxygen out of the sensing cavity. The present invention is also directed, in an alternative preferred embodiment, to such an in-situ method of oxygen removal, and the design and fabrication of a sensor device according to such principles.

It has been determined that for optimum sensing of oxides of nitrogen, and optimum suppression of interfering detection of reaction (reaction with) oxygen, the sensing electrode base material should be palladium, although other noble metals such as silver, platinum, iridium, and rhodium, and electronically conducting oxides such as perovskites (LSCo or LSM), certain bronzes, etc., can be utilized to make sensing electrode base layers. The process of fabricating the sensing electrode can play an important role in sensor performance. It has been found that baking the electrolyte pellets and sensing electrodes in a belt-furnace can produce strong bonding of the electrode material to the ceramic electrolyte pellets, reducing the impedance between the electrodes and the electrolyte, improving the sensor signal and the useful life of the sensors.

Figure 17A:
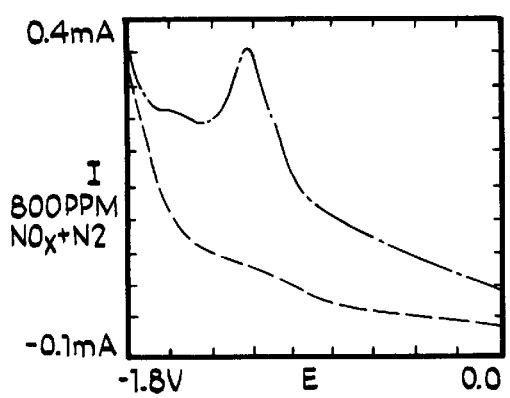
FIG. 17A is current vs. voltage response of a prototype $NO_X$ sensor for a gas mixture containing 800 ppm of NO and balance nitrogen.
Figure 17B:
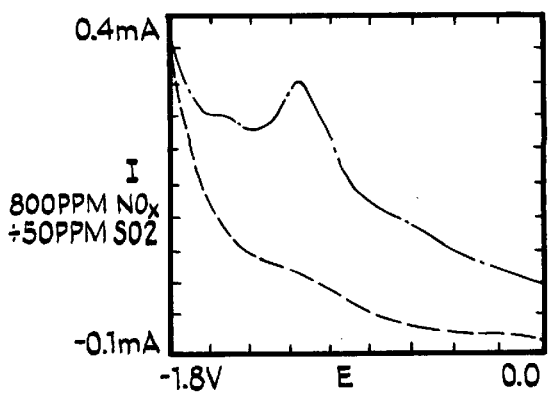
FIG. 17B is current vs. voltage response of a prototype $NO_X$ sensor for a gas mixture containing 800 ppm of NO, 50 ppm $SO_2$, and balance nitrogen.
Figure 18A:
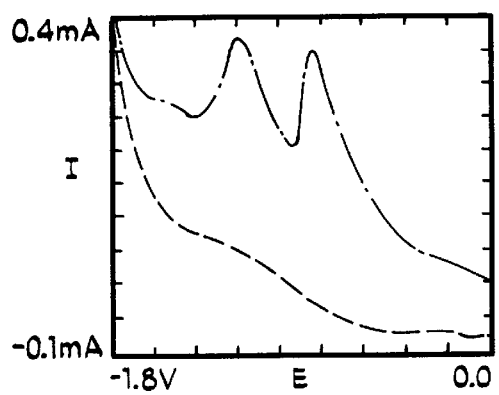
FIG. 18A is current vs. voltage response of a prototype $NO_X$ sensor for a gas mixture containing 800 ppm of NO, 1% $O_2$, and balance nitrogen.
Figure 18B:
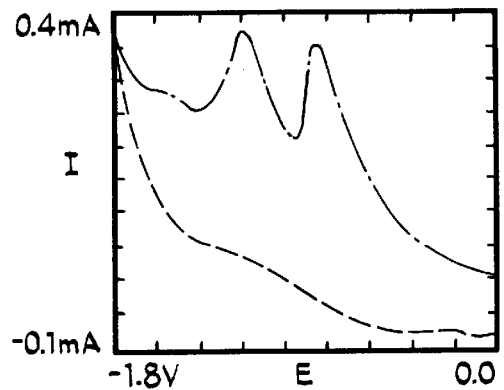
FIG. 18B is current vs. voltage response of a prototype $NO_X$ sensor for a gas mixture containing 800 ppm of NO, 1% $O_2$, 50 ppm $SO_2$, and balance nitrogen.
Figure 18C:
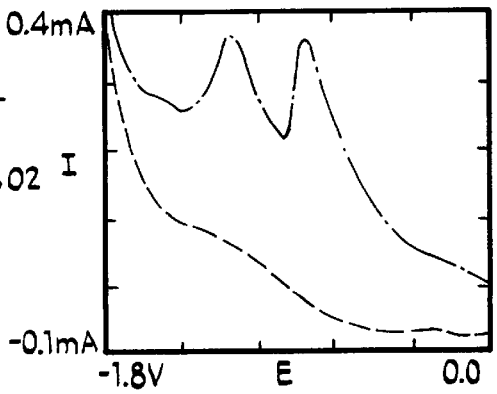
FIG. 18C is current vs. voltage response of a prototype $NO_X$ sensor for a gas mixture containing 800 ppm of NO, 1% $O_2$, 100 ppm $SO_2$, and balance nitrogen.
Figure 13A:
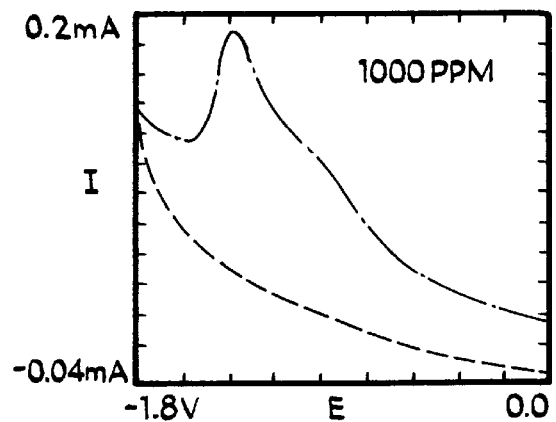
FIG. 13A is current vs. voltage response of a prototype $NO_X$ sensor for a gas mixture containing 1000 ppm of $NO_2$ and balance nitrogen.
Figure 13B:
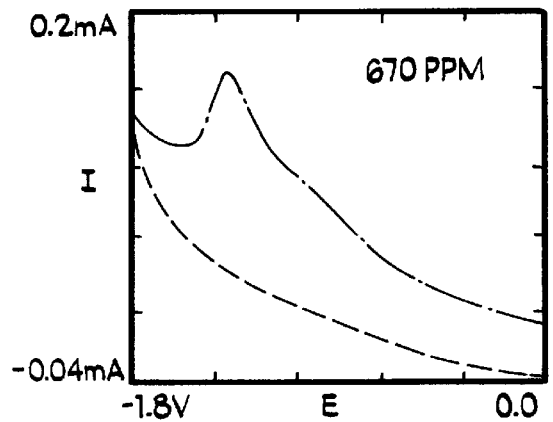
FIG. 13B is current vs. voltage response of a prototype $NO_X$ sensor for a gas mixture containing 670 ppm of $NO_2$ and balance nitrogen.
Figure 13C:
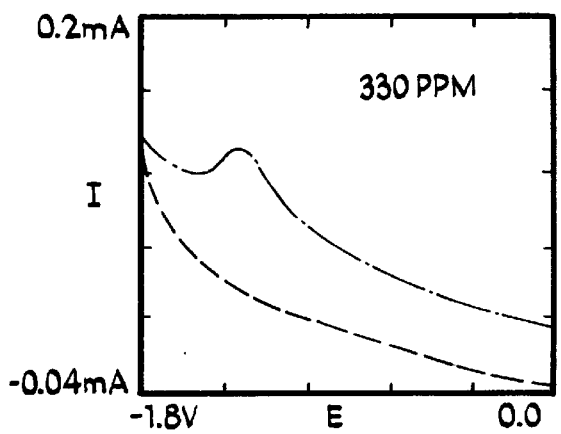
FIG. 13C is a current vs. voltage response of a prototype $NO_X$ sensor for a gas mixture containing 330 ppm of $NO_2$ and balance nitrogen.
Figure 13D:
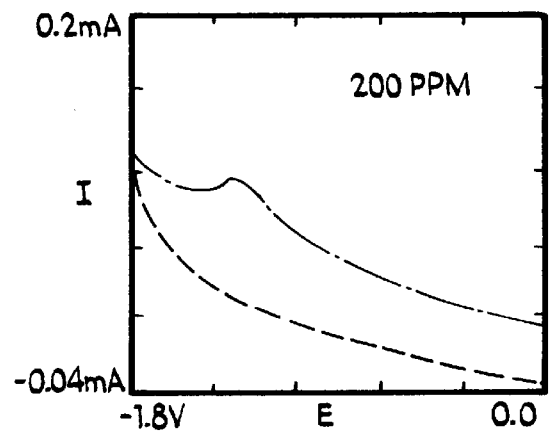
FIG. 13D is current vs. voltage response of a prototype $NO_X$ sensor for a gas mixture containing 200 ppm of $NO_2$ and balance nitrogen.
Figure 14A:
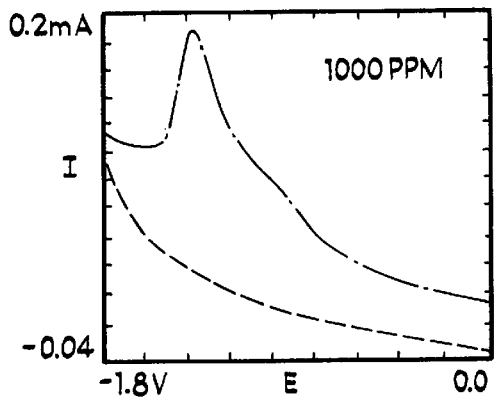
FIG. 14A is current vs. voltage response of a prototype $NO_X$ sensor for a gas mixture containing 1000 ppm of NO and balance nitrogen.
Figure 14B:
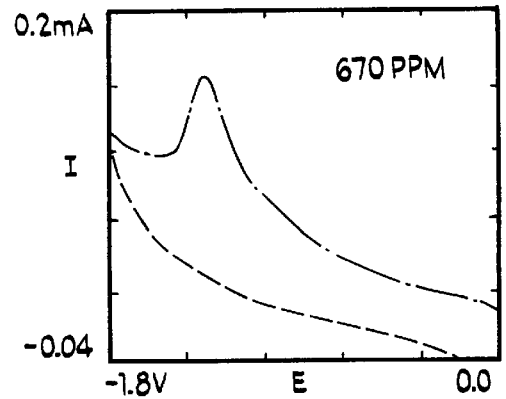
FIG. 14B is current vs. voltage response of a prototype $NO_X$ sensor for a gas mixture containing 670 ppm of NO and balance nitrogen.
Figure 14C:
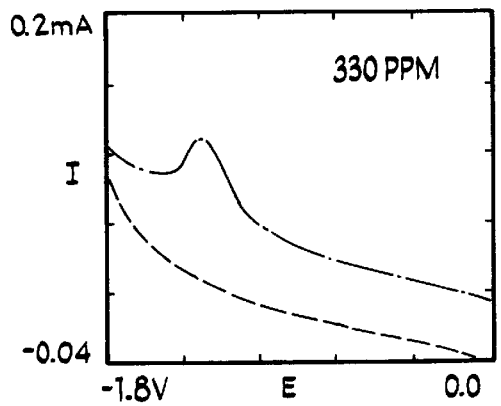
FIG. 14C is current vs. voltage response of a prototype $NO_X$ sensor for a gas mixture containing 330 ppm of NO and balance nitrogen.
Figure 14D:
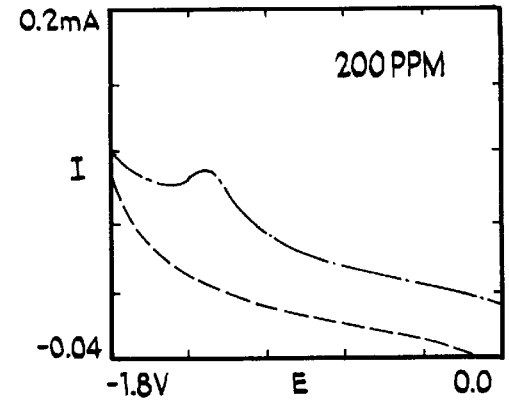
FIG. 14D is current vs. voltage response of a prototype $NO_X$ sensor for a gas mixture containing 220 ppm of NO and balance nitrogen.
Figure 14E:
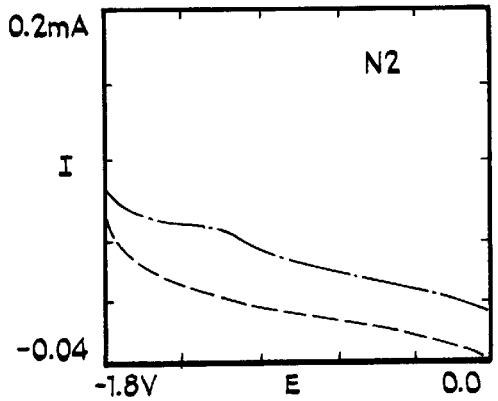
FIG. 14E is current vs. voltage response of a prototype $NO_X$ sensor for a gas mixture containing only nitrogen.
Figure 16A:
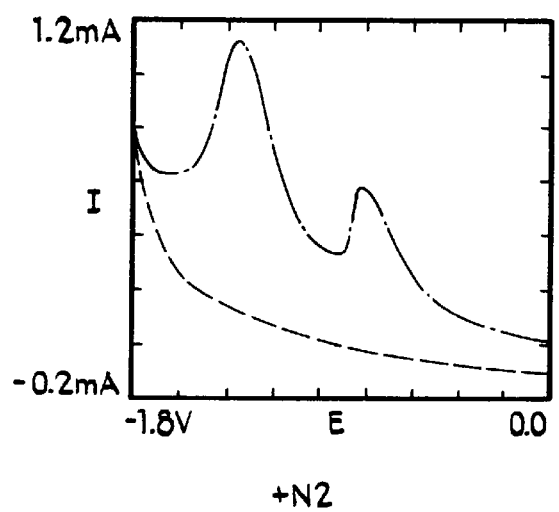
FIG. 16A is current vs. voltage response of a prototype $NO_X$ sensor for a gas mixture containing 500 ppm of NO, 1% $O_2$, and balance nitrogen.
Figure 16B:
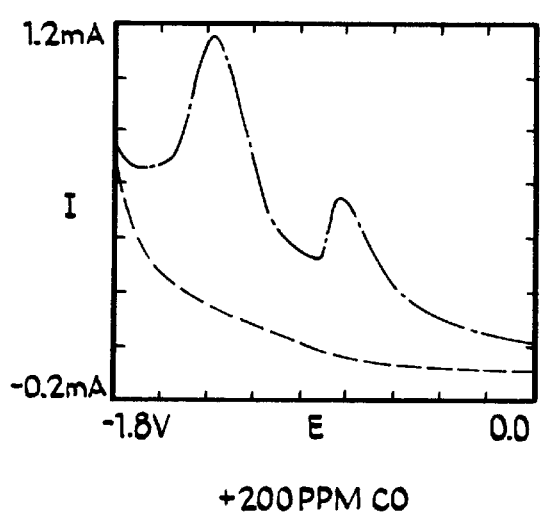
FIG. 16B is current vs. voltage response of a prototype $NO_X$ sensor for a gas mixture containing 500 ppm of NO, 1% $O_2$, 200 ppm of CO, and balance nitrogen.
Figure 16C:
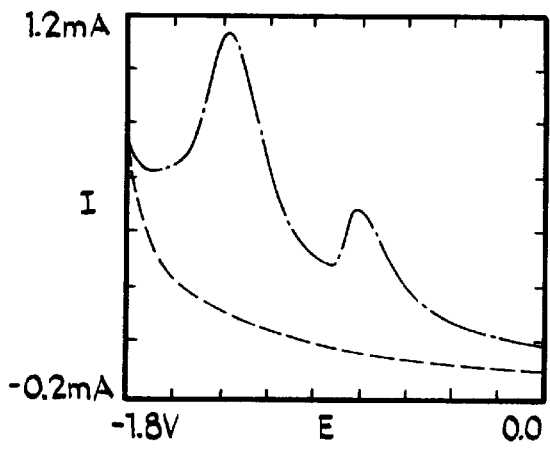
FIG. 16C is current vs. voltage response of a prototype $NO_X$ sensor for a gas mixture containing 500 ppm of NO, 1% $O_2$, 200 ppm of $CH_4$, and balance nitrogen.
Figure 16D:
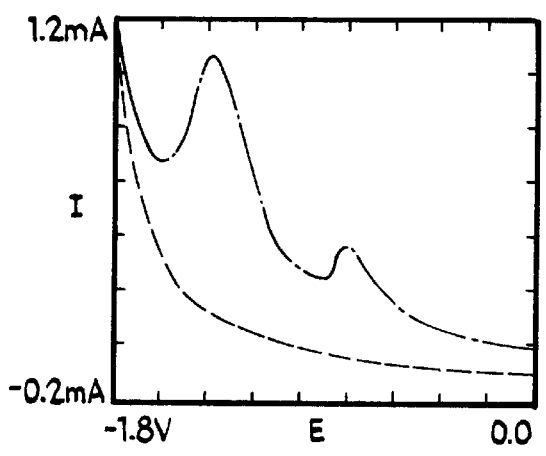
FIG. 16D is current vs. voltage response of a prototype $NO_X$ sensor for a gas mixture containing 500 ppm of NO, 1% $O_2$, with 5% $CO_2$, and balance nitrogen.

The configuration of the sensor 200 illustrated in FIG. 12 has been found to have excellent sensitivity to nitric oxide (NO) and nitrogen dioxide ($NO_2$), but not to nitrous oxide ($N_2O$), as illustrated in FIGS. 13A–D, 14A–E, and 15. The peak position for reduction of NO and $NO_2$, and the sensitivity to both gases is the same, which is desirable since it will detect the total amount of nitrogen oxides in the engine exhaust gas. The interference from other gases such as CO, $CO_2$, and $CH_4$ has also been evaluated. As shown in FIGS. 16A–D, no obvious effect on $NO_X$ measurement has been observed. The interference of $SO_2$ was examined by introducing 50 ppm of $SO_2$ into a gas mixture containing 800 ppm $NO_X$ and nitrogen. The $SO_2$ exhibited an effect on the performance of the sensor by reducing the $NO_X$ signal as shown in FIGS. 17A–B. When $SO_2$ was added to gas mixtures containing $NO_X$ and oxygen, the effect was eliminated as shown in FIGS. 18A–C. Introducing 50–100 ppm $SO_2$ into a gas mixture containing 800 ppm $NO_X$ and 1% $O_2$ shows negligible change in the $NO_X$ signal. Since small amounts of oxygen will always be present in an actual i.c. engine exhaust, the influence of $SO_2$ on sensor performance is not detrimental.

FIG. 19 schematically illustrates an oxygen remover of the type which can be used to remove oxygen from the gas stream prior to the stream reaching the gas sensor. Remover 300 includes a ceramic tube 310 which is preferably fabricated from the electrolyte material, and serves the same function. The ceramic electrolyte can be fabricated from zirconia, ceria or other oxygen ion conductors. Two cylindrical electrodes 315 and 320 are arranged on the inner and the outer surfaces 325, 330 of tube 310. Electrodes 315 and 320 may be fabricated from noble metals or perovskite materials, such as discussed with respect to the electrodes for the sensor itself.

When a negative terminal of a d.c. voltage source is connected to the inside electrode 315, oxygen will be reduced at the inside electrode and the oxygen ions will be electrochemically "pumped" radially outward of the tube. An oxygen sensor 330, of otherwise known configuration, can be attached to tube 310, at a position down stream of the oxygen pump portion of tube 310, which can measure the residual oxygen concentration after the remover has acted on the gas stream. Sensor 330 can be used for the measurement of oxygen in the gas stream (when the remover is not being operated), and can also be used as a feedback signal to control the operation of the oxygen remover (when operated at the same time as the remover), by passing its signal to a suitably connected and programmed controller (e.g., when the sensor senses oxygen concentrations above a set value, greater voltage is applied to the remover, etc.).

FIGS. 20 and 21 illustrate sensor response in gas mixtures containing oxygen, without and with oxygen pump operating.

FIG. 22 illustrates a potential configuration for an analyzer combination of a $NO_X$ sensor with an oxygen remover. Analyzer 400 includes tube 410, with oxygen remover 420. Furnace 430 heats remover section 420 up to a suitable working temperature, such as 725° C. Oxygen sensor 440 may also be provided in tube 410, as previously discussed. Tube 410 then exits furnace 430, and reenters, ending in $NO_X$ sensor 450. After passing through sensor 450, the gas stream is then exited to atmosphere, for example, so as to enable a continuous flow of gas to be sampled.

A further illustration of sensor 450 is provided in FIG. 23, in which the reference numerals of FIG. 12 have been utilized to indicate substantially identical elements. Sensor 450 is mounted onto a zirconia supporting tube 460 which may be attached to a supporting housing (not shown) by a high-pressure resistant air-tight union 470. Diffusion barrier 230 is directly glassed onto tube 460, while electrolyte 210 is exposed to the outside ambient air. Sensing electrode 215 faces the sampling gas while counter electrode 220 is exposed to the ambient air. Gas inlet tube 480, which may be a part of or attached to tube 410 (from FIG. 22) extends to a position immediately adjacent aperture 240, since the resultant "injection" of sampling gas improves response time. FIG. 24 illustrates the results of sensor performance in a stream of exhaust gas from a natural gas combustion engine. Varying air/fuel ratios and varying $NO_X$ concentrations were employed.

An alternative method for removing oxygen is illustrated in FIG. 25. An additional electrochemical cell can be incorporated into the sensor for pumping oxygen directly out of the sensing cavity.

Sensor 500 comprises electrolyte 510, having sensing electrode 515, and counter electrode 520 as discussed with respect to the previous embodiment. Glass seal/spacer 530 and diffusion barrier 535 define the sensing cavity 540 over sensing electrode 515.

Diffusion barrier 535 is fabricated from oxygen ionic conductive materials such as zirconia or ceria. Two electrodes 545, 550 are coated on both sides of barrier 535. Electrodes 545, and 550 may be fabricated from platinum or other suitable noble metals. When a negative potential is applied to the electrode 545 inside the cavity, oxygen is pumped out of the cavity 540.

Since the volume of the cavity is small (on the order of 0.002 $in^3$), the oxygen pumping can be performed efficiently. In addition, the design of FIG. 25 does not require an extra furnace for heating of the pump, as in the previously discussed embodiment. Also, there is lower power consumption, and less space is required, enabling this sensor configuration to be advantageously employed in the environment of an automobile engine exhaust system.

FIG. 26 illustrates the response of the sensor to various concentrations of $NO_X$ in an atmosphere containing 15% oxygen. It is understood that during the actual sensing, the oxygen concentration in the cavity, although not negligible, has been reduced as it is separately pumped out. As can be seen, as low as 50 ppm of $NO_X$ can be easily detected.

FIG. 27 of the drawings illustrates another embodiment of the oxygen removing means. In such an embodiment, the exhaust gas is passed through a tubular member 610 containing fine copper metal turnings 620. These metal turnings serve to getter oxygen, prior to the exhaust gas coming into contact with the sensing electrode of the sensor. The copper turnings can be periodically regenerated by passing a reducing gas such as hydrogen.

The foregoing description and drawings merely explain and illustrate the invention, and the invention is not limited thereto except insofar as the appended claims are so limited, as those skilled in the art who have the disclosure before them will be able to make modifications and variations therein without departing from the scope of the invention.

What is claimed is:

1. A sensor device for sensing gaseous oxides of nitrogen in an exhaust stream from a combustion system comprising:

a solid electrolyte membrane fabricated from an oxygen ion conducting material, the electrolyte member having two sides, with a first side of the two sides being positionable toward the exhaust stream, and a second of the two sides being positionable away from and in an isolated manner relative to the exhaust stream;

a sensing electrode operably associated with the first side of the electrolyte membrane, and in fluid communication with the exhaust stream;

catalyst material, operably disposed on the sensing electrode, and capable of catalyzing a reduction on nitrogen oxide;

a counter electrode operably associated with the second side of the electrolyte membrane;

a diffusion barrier, overlying the sensing electrode, the diffusion barrier being substantially impervious to the transport of gaseous nitrogen oxide therethrough, so as to substantially preclude uncontrolled contact between the exhaust stream and the sensing electrode;

a diffusion aperture, having desired dimensions, extending through the diffusion barrier, from the exhaust stream to the sensing electrode, for permitting controlled access and contact of gaseous components from the exhaust stream to the sensing electrode;

means for applying a potential difference between the sensing electrode and the counter electrode for enabling application of a desired electrical potential difference across the sensing electrode and the counter electrode;

means for measuring the current between the sensing electrode and the counter electrode; and means for substantially removing oxygen from the exhaust stream, operably disposed in a gas transporting relationship between the exhaust stream and the diffusion barrier, wherein the oxygen removing means includes:

a tubular member, operably disposed such that gasses in the exhaust stream are constrained to travel throughout the tubular member in order to arrive at the sensing electrode; and a material, disposed within the tubular member, which is capable of gettering oxygen, in quantity sufficient to remove molecular oxygen from the exhaust gas which will come into contact with the sensing electrode of the sensor.

2. The sensor device according to claim 1, wherein the gettering material comprises copper turnings.

* * * * *